United States Patent [19]

Evans et al.

[11] Patent Number: 5,274,077
[45] Date of Patent: Dec. 28, 1993

[54] RETINOIC ACID RECEPTOR COMPOSITION

[75] Inventors: Ronald M. Evans, La Jolla; Estelita S. Ong; Prudimar S. Segui, both of San Diego; Catherine C. Thompson, La Jolla; Kazuhiko Umesono, San Diego, all of Calif.; Vincent Giguere, Etobicoke, Canada

[73] Assignee: The Salk Institute for Biological Studies, La Jolla, Calif.

[21] Appl. No.: 975,777

[22] Filed: Nov. 13, 1992

Related U.S. Application Data

[60] Division of Ser. No. 546,256, Aug. 6, 1990, Pat. No. 5,171,671, which is a division of Ser. No. 276,536, Nov. 30, 1988, Pat. No. 4,981,784, which is a continuation-in-part of Ser. No. 128,331, Dec. 2, 1987, abandoned.

[51] Int. Cl.$^5$ .................. C07K 13/00; C12N 15/12
[52] U.S. Cl. .................. 530/350; 530/358; 435/69.1; 435/252.3
[58] Field of Search .............. 530/350, 358; 435/69.7, 435/252.3

[56] References Cited

PUBLICATIONS

Nature 330:420–21, (Dec. 3, 1987) Robertson Towards a biochemistry of morphogenesis.
Nature 330:444–450, Dec. 3, 1987) Petkovich et al. A human retinoic acid receptor which belongs to the family of nuclear receptors.
Nature 330:624–629 (Dec. 17, 1987) Giguere et al. Identification of a receptor for the morphorgen retinorc acid.

Primary Examiner—Robert J. Hill, Jr.
Assistant Examiner—John D. Ulm
Attorney, Agent, or Firm—Pretty, Schroeder, Brueggemann & Clark

[57] ABSTRACT

A novel retinoic acid receptor is disclosed. The novel receptor is encoded for by cDNA carried on plasmid phRAR1, which has been deposited with the American Type Culture Collection for patent purposes. Chimeric receptor proteins are also disclosed. The chimera are constructed by exchanging functional domains between the glucocorticoid, the mineralocorticoid, the estrogen-related, the thyroid and the retinoic acid receptors. In addition, a novel method for identifying functional ligands for receptor proteins is disclosed. The method, which takes advantage of the modular structure of the hormone receptors and the idea that the functional domains may be interchangeable, replaces the DNA-binding domain of a putative novel receptor with the DNA-binding domain of a known receptor such as the glucocorticoid receptor. The resulting chimeric construction, when expressed in cells, produces a hybrid receptor whose activation of a ligand—(e.g., glucocorticoid) inducible promoter is dependent on the presence of the new ligand. The novel method is illustrated in part by showing that the ligand for the new receptor protein is the retinoid, retinoic acid.

14 Claims, 12 Drawing Sheets

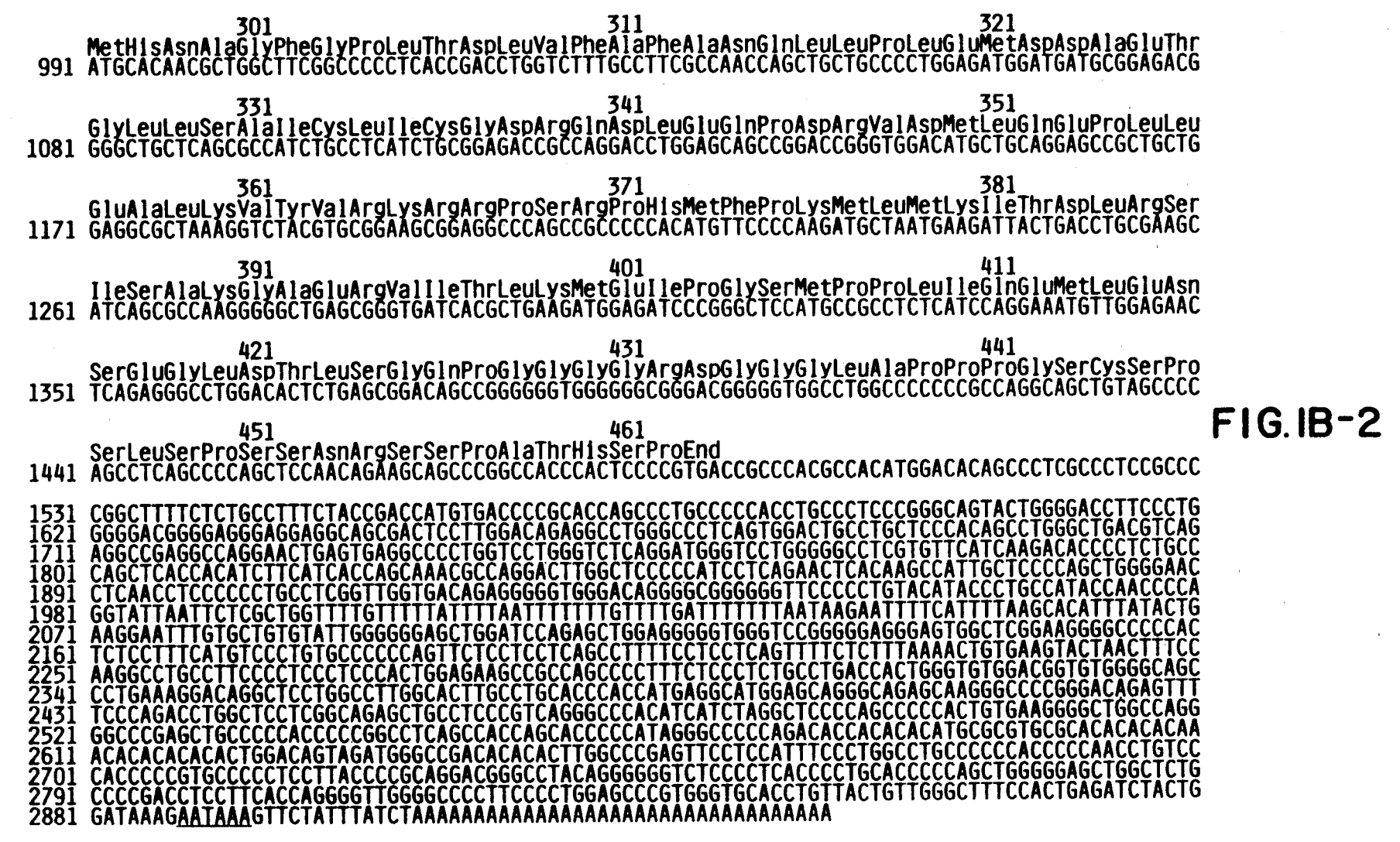

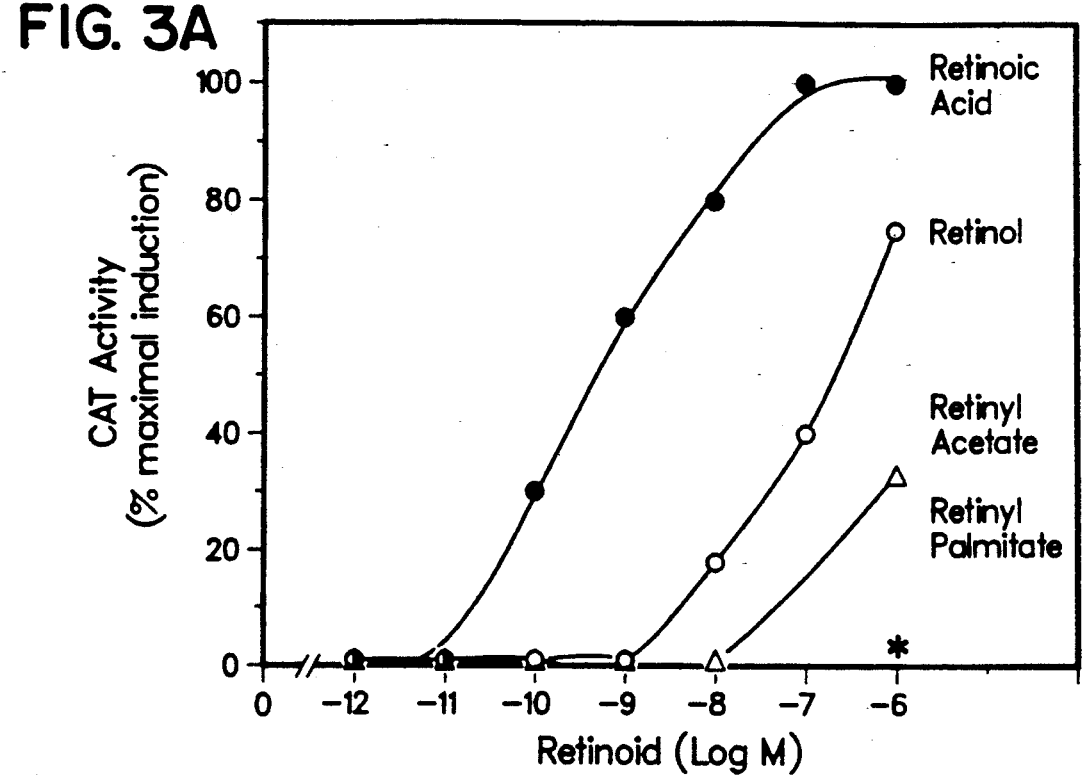
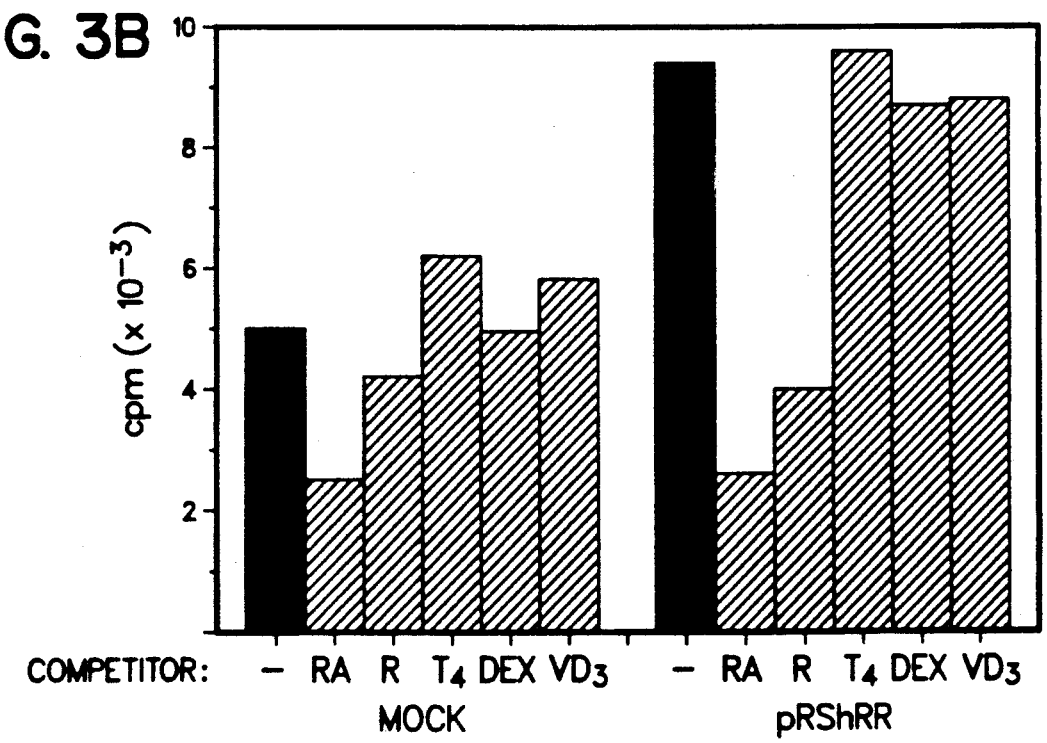

FIG.5
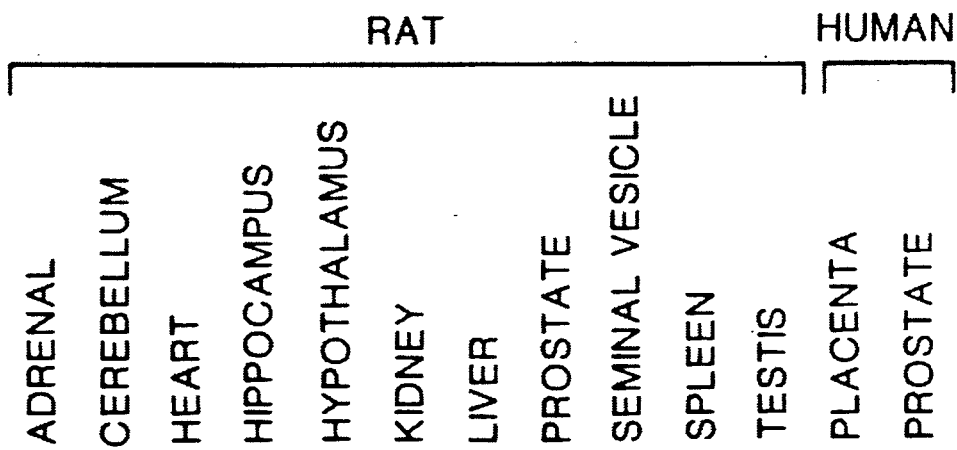
28S-
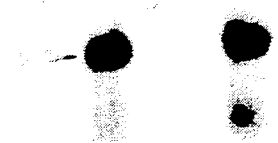
18S-

|  | HRE | DNA BINDING | HORMONE BINDING IN VITRO | HORMONE BINDING IN VIVO | TRANS-ACTIVATION | CHROMO-SOME | SPECIES |
|---|---|---|---|---|---|---|---|
| GR | +[15-19] | +[16,17,21] | +[26,82] | +[48,52,77] | +[48,52,78,79] | 5[26] | h,[26] r,[77] m[78] |
| MR | nd | nd | nd | +[36] | +[36] | 4[36] | h[36] |
| PR | +[24,34] | +[24,34] | nd | nd | +[34] | 11[79] | rabbit,[32] h,[33] c,[34] |
| ER | +[22,23] | +[23,62] | nd | +[23,53,62] | +[53,62] | 6[62] | h,[29] c,[30] frog[31] |
| ERR1 | nd | nd | nd | nd | nd | nd | h[39] |
| ERR2 | nd | nd | nd | nd | nd | nd | h[39] |
| VDR | nd | nd | nd | +[35] | nd | nd | h,[35] c[35] |
| T$_3$R$_\beta$ | +[25] | +[25] | +[37] | nd | +[80] | 3[37] | h[37] |
| T$_3$R$_\alpha$ | nd | nd | +[38,40] | nd | +[80] | 17[40] | r,[40] h,[41] c[38] |
| V-erb A | + | + | (−)[38] | nd | nd | virus | c[28] |
| RAR | nd | nd | nd | +[42,43] | +[42,43] | 17[83] | h[42,43] |
| HAP | nd | nd | nd | nd | nd | 3[45] | h[45] |
| E75 | nd | nd | nd | nd | nd |  | d[46] |

RETINOIC ACID RECEPTOR COMPOSITION

ACKNOWLEDGMENT

This invention was made with government support under a grant from the National Institutes Health (Grant No. GM 26444).

This is a divisional application of Ser. No. 546,256, filed Aug. 6, 1990, issued Dec. 15, 1992, as U.S. Pat. No. 5,171,671, which was, in turn a division of U.S. Pat. No. 276,536, filed Nov. 30, 1988, issued Jan. 1, 1991, as U.S. Pat. No. 4,981,784, which in turn, was a continuation-in-part of U.S. Ser. No. 128,331, filed Dec. 2, 1987, now abandoned.

FIELD OF THE INVENTION

The present invention relates generally to ligand-responsive regulatory proteins and genes encoding them. More particularly, the present invention relates to retinoid related regulatory proteins and genes encoding them, modification of these and other regulatory proteins and genes by recombinant DNA and other genetic engineering techniques, plus uses of the retinoid related regulatory proteins and genes, both unmodified and modified.

In addition the invention relates to a novel method for identifying functional ligands for ligand-responsive proteins. This method is especially useful for identifying functional ligand(s) for newly discovered receptor proteins. The method is exemplified in part by showing that a vitamin A related morphogen, retinoic acid, is a functional ligand for a newly discovered retinoid receptor protein.

BACKGROUND OF THE INVENTION

A central problem in eukaryotic molecular biology continues to be elucidation of molecules and mechanisms that mediate specific gene regulation in response to exogenous inducers such as hormones or growth factors. Although much remains to be learned about the specifics of such mechanisms, it is known that exogenous inducers such as hormones modulate gene transcription by acting in concert with intracellular components, including intracellular receptors and discrete DNA known as hormone response elements or HRE's.

More specifically, it is known that hormones like the glucocorticoid and thyroid hormones enter cells by facilitated diffusion. It is also known that the hormones then bind to specific receptor proteins, thereby creating a hormone/receptor complex. The binding of hormone to the receptor is believed to initiate an alosteric alteration of the receptor protein. As a result of this alteration, it is believed that the hormone/receptor complex is capable of binding with high affinity to certain specific sites on the chromatin DNA. Such sites, which are referred to in the art by a variety of names, including hormone response elements or HRE's, modulate expression (transcription of RNA) of nearby target gene promoters.

A major obstacle to further understanding the specifics of gene regulation by exogenous inducers such as hormones has been the lack of availability of receptor proteins in sufficient quantity and purity to allow such proteins to be adequately analyzed and characterized. This same lack of availability has thwarted the use of receptors in diagnostic assays to determine the presence of exogenous inducers (e.g., the hormones) in various body fluids and tissues, as well as their use as "proto- types" for engineering chimeric receptor protein analogs.

In an effort to overcome this lack of availability of receptor proteins, co-pending, application U.S. Ser. No. 108,471 now U.S. Pat. No. 5,071,773, which has been assigned to the Salk Institute for Biological Studies, assignee of the present application, discloses cloned genes for a variety of receptor proteins, including glucocorticoid-, thyroid-, mineralocorticoid- and new steroid-related receptors. U.S. Ser. No. 108,471, now U.S. Pat. No. 5,071,771, further discloses detailed biochemical characterization of these molecules which shows that the receptor proteins contain discrete DNA- and ligand-binding domains. (Portions of U.S. Ser. No. 108,471, now U.S. Pat. No. 5,071,773, have been published; for portions relating to cloning of the glucocorticoid receptor and characterization of this molecule into discrete domains, see Hollenberg, el al. (1985) and Giguere, et al., (1986); for other related work regarding receptors, see Hollenberg, et al., (1987), Green, et al., (1986), Green and Chambon, (1987), Kumar, et al., (1987), Miesfeld, et al., (1987) and Evans (1988)).

Further with regard to biochemical characterization of the receptors, sequence analysis of the human glucocorticoid receptor gene revealed homology with the product of the v-erb-A oncogene of avian erythroblastosis virus (AEV) (see Weinberger, et al., (1985)). This group and others subsequently demonstrated the cellular homolog of v-erb-A to be the beta thyroid hormone receptor (see Weinberger et al., (1986) and Sap, et al., (1986)).

The discovery that the DNA-binding domain of the steroid and thyroid hormone receptors is highly conserved raised the question of whether this segment might be diagnostic for related ligand inducible transcription factors. It also raised the question of whether the DNA sequences encoding these domains might be used as hybridization probes to scan the genome for related, but novel, ligand-responsive receptors. Utilizing this approach, our group at the Salk Institute has identified several new gene products. As is shown in U.S. Ser. No. 108,471, one is the human aldosterone receptor (hMR, ATCC No. 67201) (see Arriza, et al. , (1987) for the published version of this portion of U.S. Ser. No. 108,471, now U.S. Pat. No. 5,071,773,); a second is a novel thyroid hormone receptor expressed at high levels in the rat central nervous system (rTR alpha, ATCC No. 67281) (see Thompson, et al. , (1987) for the published version of this portion of U.S. Ser. No. 108,471, now U.S. Pat. No. 5,071,773).

This disclosure describes the isolation and characterization of a cloned full-length CDNA encoding a novel retinoid receptor protein with homology to the DNA-binding and ligand-binding domains of the steroid and thyroid hormone receptors. In addition the construction and characterization of chimeric receptors made by "swapping" functional domains between the glucocorticoid, the mineralocorticoid, the thyroid, the estrogen-related, and the retinoic acid receptors is described. These chimeric receptors have hybrid functional characteristics based on the florigin"of the "parental" DNA-binding and ligand-binding domains incorporated within the chimeras. For example, if the DNA-binding domain in the chimeric receptor is a retinoic acid receptor DNA-binding domain (i.e., is obtained from wild-type retinoic acid receptor or is a mutant that contains the functional elements of retinoic acid DNA-binding domain), then the chimera will have DNA-binding properties characteristic of a retinoic acid receptor. The same is true of the ligand-binding domain. If the ligand-binding domain in the chimeric receptor binds to thyroid hormone, then the chimera will have ligand-binding properties characteristic of a thyroid hormone receptor.

This disclosure also describes a new method for identifying functional ligands for ligand-responsive receptor proteins. The method is illustrated by showing (1) that the retinoid, retinoic acid and its metabolic precurser, retinol, are functional ligands for the newly discovered receptor protein, and (2) that the DNA- and ligand-binding domains determine the functional characteristics of the chimeric receptors.

BRIEF DESCRIPTION OF THE DRAWINGS

The following is a brief description of the drawings. More detailed descriptions are found in the section of the specification labeled, "Detailed Description of the Drawings".

FIG. 1 (A and B) is a drawing which shows the DNA nucleotide sequence and the primary protein sequence of phRARα. FIGS. 1B-1 and 1B-2 show the complete nucleotide sequence of phRARα and its primary amino acid sequence.

FIG. 2 (A and B) is composed of a drawing and a blot.

FIG. 3 (A and B) is composed of two graphs. FIG. 3A is a graph illustrating dose-response to retinoids. FIG. 3B is a bar graph illustrating retinoic acid binding to cytosol extracts of transfected COS-1 cells.

FIG. 4 (A and B) shows a Southern blot analysis of human genomic DNA.

FIG. 5 shows a Northern blot analysis of retinoic acid receptor MRNA in rat and human tissues.

FIG. 8(1 and 2) is a schematic drawing that shows amino acid comparison of members of the steroid hormone receptor superfamily.

DEFINITIONS

Figure 1A:
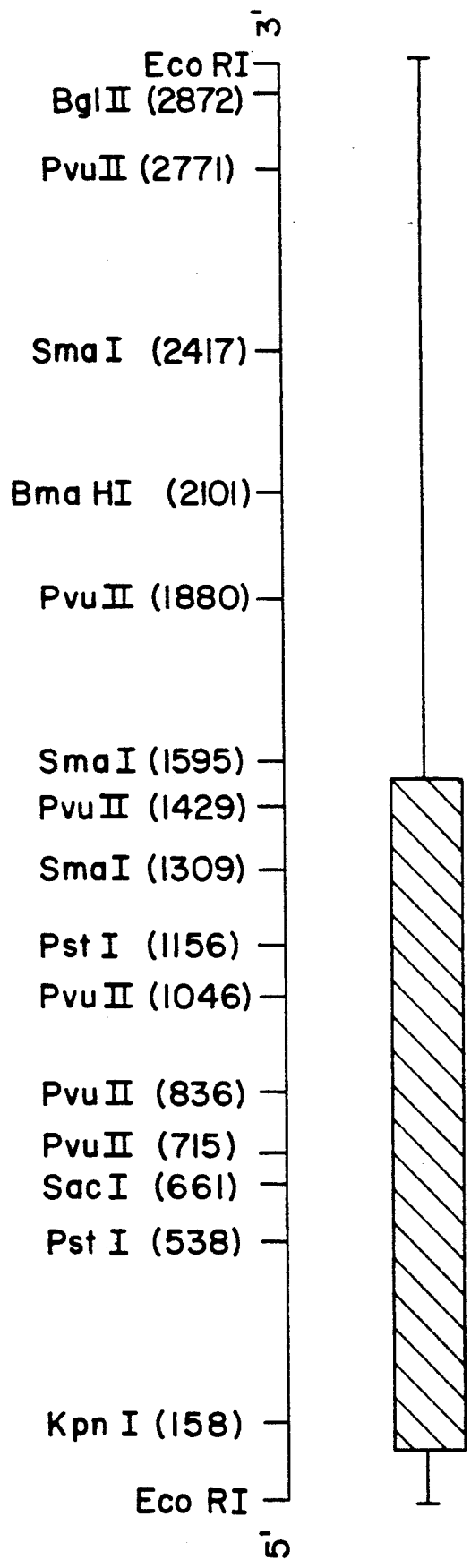
FIG. 1A shows the composite structure of phRARα aligned with a line diagram of some restriction endonuclease cleavage sites.

In the present specification and claims, reference will be made to phrases and terms of art which are expressly defined for use herein as follows:

As used herein, the generic term "retinoids" means a group of compounds which includes retinoic acid, vitamin A (retinol) and a series of natural and synthetic derivatives that can exert profound effects on development and differentiation in a wide variety of systems.

As used herein, species are identified as follows: h, human; r, rat; m, mouse; c, chicken; and d, Drosophilia.

As used herein, "steroid hormone superfamily of receptors" refers to the class of related receptors comprised of glucocorticoid, mineralocorticoid, progesterone, estrogen, estrogen-related, vitamin D$_3$, thyroid, v-erb-A, retinoic acid and E75 (Drosophilia) receptors. See Evans (1988) and the references cited therein.

As used herein, RR and RAR both mean retinoic acid receptor. The acronyms, hRR and hRAR, mean human retinoic acid receptor. The DNA referred to as phRARα codes for human retinoic acid receptor alpha. hRARα is encoded by deposited phRAR1 which has been accorded ATCC No. 40392. The DNA referred to as hRAPβ encodes human retinoic acid receptor beta. See Brand et al. , (1988)

As used herein, GR means glucocorticoid receptor. The DNA referred to as hGR codes for human glucocorticoid receptor GR. hGR is encoded by deposited pRShGR which has been accorded ATCC No. 67200.

As used herein, MR means mineralocorticoid receptor. The DNA referred to as hMR codes for human mineralocorticoid receptor MR. hMR is encoded by deposited pRShMR which has been accorded ATCC No. 67201.

As used herein, TR means thyroid receptor. TRalpha and TRbeta refer to the alpha and beta forms of the thyroid receptor. The DNA's referred to as c-erb-A, herb-A 8.7, peA101, rbeAl2, and hFA8 all code for thyroid receptors. Plasmid pherb-A 8.7 encodes hTRα; it has been deposited for patent purposes and accorded ATCC No. 40374. Plasmid peA101 encodes HTPβ; it has been deposited for patent purposes and accorded ATCC No. 67244. Plasmid rbeAl2 encodes rTRα; it has been deposited for patent purposes and accorded ATCC No. 67281. Plasmid phFA8 encodes a partial clone of HTRα that has a deletion in the "ligand-binding" region of the clone (i.e., the DNA that codes for the carboxy terminal end of the receptor protein). Plasmid phFA8 has been accorded ATCC No. 40372.

As used herein, ERR means estrogen-related receptor. The acronyms, hERR1 and hERR2 refer to human estrogen-related receptors 1 and 2. These receptors are more related to steroid receptors than to the thyroid receptors, yet they do not bind any of the major classes of known steroid hormones (Giguere, et al, 1988) . hERR1 is encoded by deposited plasmids pE4 and pHKA, which have been accorded ATCC Nos. 67309 and 67310, respectively. (Neither pE4 or pHKA are complete clones; hERR1 is constructed by joining segments from both clones.) hERR2 is encoded by deposited plasmid phH3 which has been accorded ATCC No. 40373.

As used herein, VDR means vitamin D$_3$ receptor.

As used herein, MTV means mammary tumor virus; MMTV means mouse mammary tumor virus.

As used herein, RSV means Rous sarcoma virus; SV means Simian virus.

As used herein, CAT means chloramphenicol acetyltransferase.

As used herein, luciferase means firefly luciferase. See, de Wet, I. R., Wood, K. V., DeLuca, M., Helinski, D. R. , and Subramani, S., Mol. Cell. Biol. 7: 725-737 (1987).

As used herein, COS means monkey kidney cells which express T antigen (Tag) . See Gluzman, Cell, 23:175 (1981). COS cells are receptor-deficient cells that are useful in the functional ligand identification assay of the present invention.

As used herein, CV-1 means mouse kidney cells from the cell line referred to as "CV-1". CV-1 is the parental line of COS. Unlike COS cells, which have been transformed to express SV40 T antigen (Tag), CV-1 cells do not express T antigen. CV-1 cells are receptor-deficient cells that are also useful in the functional ligand identification assay of the present invention.

As used herein, the generic terms of art, "hormone response elements" or "HRE's", "transcriptional control units", "hormone responsive promoter/enhancer elements", "enhancer-like DNA sequences" and "DNA sequences which mediate transcriptional stimulation", all mean the same thing, namely, short cis-acting sequences (about 20 bp in size) that are required for hormonal (or ligand) activation of transcription. The attachment of these elements to an otherwise hormone-nonresponsive gene causes that gene to become hormone responsive. These sequences, referred to most frequently as hormone response elements or HRE's, function in a position- and orientation-independent fashion. Unlike other enhancers, the activity of the HRE's is dependent upon the presence or absence of ligand. (See Evans (1988) and the references cited therein.) In the present specification and claims, the phrase "hormone response element" is used in a generic sense to mean and embody the functional characteristics implied by all terms used in the art to describe these sequences.

As used herein, synthetic HRE's refer to HRE's that have been synthesized in vitro using automated nucleotide synthesis machines. Since the HRE's are only about 20 bp in size, they are easily synthesized in this manner. If wild-type, engineered or synthetic HREs are linked to hormone-nonresponsive promoters, these promoters become hormone responsive. See Evans (1988) and the references cited therein.

As used herein, the acronym GRE means glucocorticoid response element and TRE means thyroid receptor response element. GRE's are hormone response elements that confer glucocorticoid responsiveness via interaction with the GR. See Payvar, et al., Cell, 35:381 (1983) and Schiedereit, el al., Nature, 304:749 (1983). GRE's can be used with any wild-type or chimeric receptor whose DNA-binding domain can functionally bind (i.e., activate) with the GRE. For example, since GR, MR and PR receptors can all activate GRE's, a GRE can be used with any wild-type or chimeric receptor that has a GR, MR or PR-type DNA-binding domain. TRE's are similar to GRE's except that they confer thyroid hormone responsiveness via interaction with TR. TRE's can be used with any wild-type or chimeric receptor whose DNA-binding domain can functionally bind (i.e., activate) with the TRE. Both TR and RR receptors can activate TRE's, so a TRE can be used with any receptor that has a TR or RR-type DNA-binding domain.

As used herein, ligand means an inducer, such as a hormone or growth substance. Inside a cell the ligand binds to a receptor protein, thereby creating a ligand/receptor complex, which in turn can bind to an appropriate hormone response element. Single ligands may have multiple receptors. For example, both the $T_3R_\alpha$ and the $T_3R_\beta$ bind thyroid hormone such as $T_3$.

As used herein, the word "operative", in the phrase "operative hormone response element functionally linked to a ligand-responsive promoter and an operative reporter gene", means that the respective DNA sequences (represented by the terms "hormone response element", "ligand-responsive promoter" and "reporter gene") are operational, i.e., the hormone response element can bind with the DNA-binding domain of receptor protein (either wild-type or chimeric), the ligand-responsive promoter can control transcription of the reporter gene (upon appropriate activation by a HRE/receptor protein/ligand complex) and the reporter gene is capable of being expressed in the host cell. The phrase "functionally linked" means that when the DNA segments are joined, upon appropriate activation, the reporter gene (e.g., CAT or luciferase) will be expressed. This expression occurs as the result of the fact that the "ligand responsive promoter" (which is downstream from the hormone response element, and "activated" when the HRE binds to an appropriate ligand/receptor protein complex, and which, in turn then "controls" transcription of the reporter gene) was "turned on" or otherwise activated as a result of the binding of a ligand/receptor protein complex to the hormone response element.

As used herein, the phrase "DNA-binding domain" of receptors refers to those portions of the receptor proteins (such as glucocorticoid receptor, thyroid receptor, mineralocorticoid receptor, estrogen-related receptor and retinoic acid receptor) that bind to HRE sites on the chromatin DNA. The boundaries for these DNA-binding domains have been identified and characterized for the steroid hormone superfamily. See FIG. 8; also see Giguere, et al., (1986); Hollenberg, et al., (1987) Green and Chambon (1987); and Miesfield, et al., (1987), Evans (1988).

The boundaries for the DNA-binding domains for various steroid hormone superfamily receptors are shown in FIG. 8(1 and 2); the boundaries are as follows:

| | |
|---|---|
| -hGR (pRShGR): | nucleotide 1393 to 1590 |
| | amino acid 421 to 486 |
| | (See ATCC #67200) |
| -hTRb (peA101): | nucleotide 604 to 807 |
| | amino acid 102 to 169 |
| | (See ATCC #67244) |
| -hTRa (pherb-A8.7): | nucleotide 168 to 372 |
| | amino acid 50 to 117 |
| | (See ATCC #40374) |
| | amino acid 291 to 358 |
| | (See ATCC #67281) |
| -ERR1 (pE4 & pHKA): | amino acid 176 to 241 |
| | (See ATCC #67309 & #67310) |
| -ERR2 (phH3): | amino acid 103 to 168 |
| | See ATCC #40373) |
| -hMR (pRShMR): | nucleotide 2029 to 2226 |
| | amino acid 603 to 668 |
| | (See ATCC #67201) |
| -hRARa phRAR1): | nucleotide 364 to 561 |
| | amino acid 88 to 153 |
| | (See ATCC #40392) |

The DNA-binding domains of the steroid hormone superfamily of receptors consist of an amino segment varying between 66 to 68 amino acids in length. This segment contains 9 cysteine residues, one of which is the first amino acid of the segment. This first Cys residue begins a motif described as Cys-$x_2$-cys-$X_{13-15}$-CyS-$X_2$-CYS, where X is any amino acid residue. The DNA-binding domain invariably ends with the amino acids Gly-Met.

For convenience in the cloning procedure, between 1 and 6 amino acid residues preceding and/or following the DNA-binding domain can be switched along with the DNA-binding domain.

As used herein, the phrase "ligand-binding domain region" of receptors refers to those portions of the receptor proteins that bind to ligands such as growth substances or hormones. These boundaries of the ligand-binding domains for the steroid receptor superfamily have been identified and characterized. See FIG. 8(1 and 2) and and (1988).

The ligand-binding domains for the various receptors are shown in FIG. 8-1; some of those domains are as follows:

| | |
|---|---|
| -hGR (pRShGR): | amino acid 528 to 777 (See ATCC #67200) |
| -hTRb (peA101): | amino acid 232 to 456 (See ATCC #67244) |
| -hTRa (pherb-A8.7): | amino acid 183 to 410 (See ATCC #40374) |
| -rTR (rbeA12) | amino acid 421 to 639 (See ATCC #67281) |
| -ERR1 (pE4 & pHKA): | amino acid 295 to 521 (See ATCC #67309) |
| -ERR2 (phH3) | amino acid 212 to 433 (See ATCC #40373) |
| -hMR (pRShMR): | amino acid 734 to 984 (See ATCC #67201) |
| -hRARa (phRAR1): | amino acid 198 to 462 (See ATCC #40392) |

Common restriction endonuclease sites must be introduced into receptor CDNA clones to allow exchange of functional domains between receptors. In any of the various receptors referred to in FIG. 8(1 and 2), the first common site can be introduced immediately preceding the DNA-binding domain, the second common site immediately following it. (For example, in any of the steroid hormone superfamily of receptors that are shown in FIG. 8(1 and 2) a unique NotI site can be introduced immediately preceding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from any one receptor can be combined with cassettes from other receptors to create a variety of chimeric receptors.

As used herein, the nomenclature used to identify the chimeric receptors is as follows: The various functional domains (N-terminus, DNA-binding and ligand-binding) are identified according to the "parental" receptor from which they originated. For example, domains from GR are "G" domains; TR domains are "T" domains (unless otherwise further specified as being "$T_a$" or "Tb" domains); MR domains are "M" domains; RAR domains are "R" domains (unless otherwise further specified as being "$R_a$" or "$R_b$" domains), and ERR domains are "E" domains (unless otherwise specified as being "$E_1$" or "$E_2$" domains). According to this notation, unless otherwise specified, "T" is used generically to mean either the $T_3R_\alpha$ or the $T_3R_\beta$ receptors; "E" means either hERR1 or hERR2; and "R" means either the RARA or the RAP$\beta$ receptors. Wild-type receptors do not contain any exchanged domains, and so according to this notation system would be identified as G-G-G (or GGG) , $T_a$-$T_a$-$T_a$ (or $T_aT_aT_a$) , $T_b$-$T_b$-$T_b$ (or $T_bT_bT_b$), M-M-M (or MMM) , $R_a$-$R_a$-$R_a$ (or $R_aR_aR_a$) , $R_b$-$R_b$-$R_b$ (or $R_bR_bR_b$), $E_1$-$E_1$-$E_1$ or $E_2$-$E_2$-$E_2$, where the first domain listed is the N-terminus domain, the middle domain is the DNA-binding domain, and the last domain is the ligand-binding domain. Any chimeric receptor will have functional domains from at least two wild-type or parental sources. For example, the chimeric receptor $GGR_a$ would have N-terminus and DNA-binding domains from glucocorticoid receptor and the ligand-binding domain from the alpha retinoic acid receptor; $GT_aR_b$ would have the N-terminus from glucocorticoid, the DNA-binding domain from thyroid receptor alpha and the ligand-binding domain from retinoic acid receptor beta.

As used herein, $hGR_{NX}$, $hTP\beta_{NX}$, and $HRR_{NX}$ refer to hGR, HTP$\beta$ and hRR receptors that have been engineered to contain the unique sites for NotI and XhoI flanking the boundaries for the DNA-binding domains in these receptors. These mutant receptors exemplify construction of hybrid receptors that are comprised of all possible combinations of amino termini, DNA-binding domains, and ligand-binding domains from hGR, hMR, hERR1, hERR2, hTR$\alpha$, HTP$\beta$, rTR$\alpha$, hRAR$\alpha$, and hRAP$\beta$.

As used herein, Southern blot analysis refers to a procedure for transferring denatured DNA from an agarose gel to a nitrocellulose filter where it can be hybridized with a complementary nucleic acid.

As used herein, Northern blot analysis refers to a technique for transferring RNA from an agarose gel to a nitrocellulose filter on which it can be hybridized to complementary DNA.

As used herein, "mutant" DNA of the invention refers to DNA which has been genetically engineered to be different from the "wild-type" or unmodified sequence. Such genetic engineering can include the insertion of new nucleotides into wild-type sequences, deletion of nucleotides from wild-type sequences, or "swapping" of functional domains from one receptor to another. Receptors that have been engineered by "swapping" functional domains from one receptor to another are also referred to as chimeric or hybrid receptors. Chimeric receptors can be further engineered to include new nucleotides, deletion of nucleotides, substitution of nucleotides, etc.

Use of the term "substantial sequence homology" in the present specification and claims means it is intended that DNA, RNA, or amino acid sequences which have slight and non-consequential sequence variations from the actual sequences disclosed and claimed herein are within the scope of the appended claims. In this regard, the "slight and non-consequential" sequence variations mean that the homologous sequences will function in substantially the same manner to produce substantially the same compositions as the nucleic acid and amino acid compositions disclosed and claimed herein.

As used herein, the term "recombinantly produced" means made using genetic engineering techniques, not merely purified from nature.

The amino acids which comprise the various amino acid sequences appearing herein may be identified according to the following three-letter or one-letter abbreviations:

| Amino Acid | Three-Letter Abbreviation | One-Letter Abbreviation |
|---|---|---|
| L - Alanine | Ala | A |
| L - Arginine | Arg | R |
| L - Asparagine | Asn | N |
| L - Aspartic Acid | Asp | D |
| L - Cysteine | Cys | C |
| L - Glutamine | Gln | Q |
| L - Glutamic Acid | Glu | E |
| L - Histidine | His | H |
| L - Isoleucine | Ile | I |
| L - Leucine | Leu | L |
| L - Lysine | Lys | K |

| Amino Acid | Three-Letter Abbreviation | One-Letter Abbreviation |
| --- | --- | --- |
| L - Methionine | Met | M |
| L - Phenylalanine | Phe | F |
| L - Proline | Pro | P |
| L - Serine | Ser | S |
| L - Threonine | Thr | T |
| L - Tryptophan | Trp | W |
| L - Tyosine | Tyr | Y |
| L - Valine | Val | V |

The nucleotides which comprise the various nucleotide sequences appearing herein have their usual single-letter designations (A, G, T, C or U) used routinely in the art.

As used herein, bp means base pairs and kb means kilobase pairs.

In the present specification and claims, the Greek letters alpha ($\alpha$), beta ($\beta$), etc. are sometimes referred to as a, b, etc.

DEPOSITS

Plasmids pRShGR (hGR), pRShMR (hMR), peA101 (hT3$\beta$) and GMCAT, all of which are in E. coli HB101, plus plasmids rebAl2 (rTR$\alpha$), pE4 and phKA (which together encode hERR1), phH3 (hERR2), pherb-A 8.7 (hTR$\alpha$), phFA 8 (a partial clone of hTR$\alpha$), and plasmid phRAR1 have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the plasmids are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The ATCC Deposit Numbers and Deposit Dates for the deposits are as follows:

| pRShGR (hGR) | 67200 | Sept. 9, 1986 |
| --- | --- | --- |
| pRShMR (hMR) | 67201 | Sept. 9, 1986 |
| pE4 (hERR1*) | 67309 | Jan. 30, 1987 |
| phHKA (hERR1*) | 67310 | Jan. 30, 1987 |
| phH3 (hERR2) | 40373 | Sept. 29, 1987 |
| GMCAT (reporter) | 67282 | Dec. 18, 1986 |
| pherb-A 8.7 (hTRa) | 40374 | Sept. 29, 1987 |
| phFA 8 (hTRa*) | 40372 | Sept. 29, 1987 |
| peA101 (hTRb) | 67244 | Oct. 22, 1986 |
| prbeA12 (rTRa) | 67281 | Dec. 18, 1986 |
| phRARa (hRARa) | 40392 | Nov. 20, 1987 |

(* means a partial clone)
(pE4 & phHKA together encode complete hERR1)

SUMMARY OF THE INVENTION

In one aspect, the present invention comprises a double-stranded DNA segment wherein the plus or sense strand of the segment contains a sequence of triplets coding for the primary sequence of a protein which has ligand-binding and DNA-binding (or transcription-activating) properties characteristic of a retinoid receptor protein referred to herein as human retinoic acid receptor protein. According to this aspect of the invention, the double-stranded DNA segment is one which is capable of being expressed into retinoic acid receptor protein.

In another aspect, the invention comprises a single-stranded DNA, which is the sense strand of a double-stranded DNA coding for retinoic acid receptor protein, and an RNA made by transcription of this double-stranded DNA.

In another aspect, the invention comprises a plasmid, phRAR1, which contains DNA coding for a retinoic acid receptor protein of the present invention (RAR$\alpha$). This plasmid has been deposited with the American Type Culture Collection for patent purposes; it has been accorded ATCC No. 40392.

In still another aspect, the invention comprises a cell, preferably a mammalian cell, transformed with a DNA coding for retinoic acid receptor protein. According to this aspect of the invention, the transforming DNA is capable of being expressed in the cell, thereby increasing the amount of retinoic acid receptor, encoded by this DNA, in the cell.

Further the invention comprises novel retinoic acid receptors made by expression of a DNA coding for retinoic acid receptor or translation of an MRNA transcribed from such a retinoic acid receptor coding DNA. According to this aspect of the invention, the retinoic acid receptors will be protein products of "unmodified" retinoic acid coding DNA's and mRNA's, or will be modified or genetically engineered retinoic acid receptor protein products which, as a result of engineered mutations in the receptor DNA sequences, will have one or more differences in amino acid sequence from the corresponding naturally occurring "wild-type" retinoic acid receptor proteins. Preferably these retinoic acid receptors, whether "unmodified" or "engineered", will have at least about 5% of the retinoic acid binding activity and/or at least about 5% of the DNA-binding or transcription-activating activity of the corresponding naturally occurring retinoic acid receptor.

Further the invention comprises chimeric receptors made by exchanging the functional domains of one receptor with functional domains of another type. The chimeric DNA's thus produced encode chimeric receptor proteins that have functional characteristics based on the "origin" of their respective DNA- and ligand-binding domains. The chimeric receptors of the invention include double-stranded DNA's that code for the chimeric receptors, as well as single-stranded DNA's which are the sense strands of the double-stranded DNA's, and mRNA's made by transcription of the double-stranded DNA's. The invention also comprises cells, both eukaryotic and prokaryotic, that are transformed with chimeric receptors encoding DNA's of the invention.

According to the chimeric receptor aspect of the invention, to effect the chimeric DNA fusions, two restriction endonuclease sites are introduced into each receptor CDNA at comparable locations in or near the DNA-binding domains in order to divide the receptor DNA's into three functional domains or regions. (For example, a unique NotI site can be introduced immediately preceding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from any one receptor can be combined with cassettes from other receptors to create a variety of chimeric receptors. This aspect of the invention is illustrated in the section of the specification labeled "Detailed Description of the Invention".)

In the present specification and claims, the chimeric receptors (referred to also as chimera or hybrids) are named by letters referring to the origin of the various domains. Domains from hGR are referred to as "G" domains, domains from hTR are "T" domains, domains from HERR are "E" and domains from hRR are "R" domains. For example, the chimeric receptor "RGR" has the amino and carboxyl termini of hRR and the DNA-binding domain of hGR; the chimeric receptor "TGG" has the amino terminus from hTR, and the DNA-binding and carboxyl terminus from hGR. (In the diagram shown in FIG. 7, the amino terminus of the receptor is referred to domain A/B and the carboxyl terminus is referred to as domain E.)

According to the notation used in the specification and claims, unless otherwise specified, "T" is used generically to mean either the $T_3R_\alpha$ or the $T_3R_\beta$ receptor; "E" means either hERR1 or hERR2; and "R" means either the RAR$\alpha$ or the RAP$\beta$ receptor.

Chimeric receptors of the invention include chimera having (1) an N-terminus domain selected from the group of wild-type receptors consisting of hGR, hMR, HERR$_1$, hERR$_2$, rTR$\alpha$, hT$_3\alpha$, hT$_3\beta$, hRAR$\alpha$ and hRAP$\beta$, (2) a DNA-binding domain selected from the group of wild-type receptors consisting of hGR, hMR, HERR$_1$, hERR$_2$, rTR$\alpha$, ht$_3\alpha$, hT$_3\beta$, hRAR$\alpha$ and hRAP$\beta$, and (3) a ligand-binding domain selected from the group of wild-type receptors consisting of hGR, hMR, hERR$_1$, hERR$_2$, rTR$\alpha$, hT$_3\alpha$, hT$_3\beta$, hRAR$\alpha$ and HRAP$\beta$, wherein any one chimeric receptors will have N-terminus, DNA-binding, and ligand-binding domains that originate from at least two different "wild-type receptor" sources.

Preferred chimeric receptor DNA's of the invention include GRR, GRG, GGR, RGG, RGR, RRG, GTT, GTG, GGT, TGG, TGT, TTG, TTR, TRT, TRR, RTT, RTR, RRT, GTT, GTG, GGT, TGG, TGT, and TTG receptor DNA's, plus the chimeric hybrid receptor proteins made by expression of a chimeric DNA of the invention or translation of an MRNA transcribed from such a chimeric receptor coding DNA. Preferably these chimeric receptors will have activity that exceeds exogenous background binding or transcriptional activation activity levels in any given cell, or will have at least about 5% of the DNA-binding or transcription-activating activity of the corresponding naturally occurring receptor DNA-binding domain, and/or about 5% of the ligand-binding activity of the corresponding naturally occurring ligand-binding domain.

The invention also comprises a method for identifying functional ligand(s) for receptor proteins. According to the method, DNA sequences (referred to herein as the sample sequences) can be isolated which code for receptor proteins and which have at least an operative portion of a ligand-binding domain and a DNA-binding domain. (As those skilled in the art will appreciate, not all of the DNA sequences in the ligand-binding domains are necessary in order for the domains to be functional. The operative sequences, i.e., those that must be present if the domain is to bind ligand, can be identified by deletion studies on any given domain.) Once the sample DNA sequences are isolated, a chimeric gene can be created by substituting the DNA-binding domain region in the sample DNA sequence with a DNA-binding domain region taken from a DNA sequence coding for another receptor protein, e.g., glucocorticoid receptor protein, thyroid receptor protein, mineralocorticoid receptor protein or retinoic acid receptor protein. Next a suitable receptor-deficient host cell is transfected with: (1) the chimeric receptor gene, which is preferably carried on an expression plasmid, and (2) a reporter gene, such as the CAT gene or the firefly luciferase gene, which is also preferably carried on plasmid, and which is referred to in U.S. Ser. No. 180,475, now U.S. Pat. No. 5,071,771, as a reporter plasmid. In any case, the repoliter gene is functionally linked to an operative hormone response element (HRE) (either wild-type or engineered) wherein the hormone response element is capable of being activated by the DNA-binding domain used to make the chimeric receptor gene. (For example, if the chimeric receptor gene contains the DNA-binding domain region from glucocorticoid receptor coding DNA, then the HRE should be a wild-type, an engineered, or a synthetic GRE, i.e., one that can be activated by the operative portion of the DNA-binding region of a glucocorticoid receptor protein. If a thyroid receptor DNA-binding domain region is used, then the wild-type or engineered HRE should be responsive to a thyroid (or retinoic acid) receptor protein, etc.) Next the transfected host cell is challenged with a battery of candidate ligands which can potentially bind with the ligand-binding domain region of the chimeric protein coded for by the chimeric gene. To determine which of these ligands can functionally complex with the chimeric receptor protein, induction of the reporter gene is monitored by monitoring changes in the protein levels of the protein coded for by the reporter gene. (For example, if luciferase is the reporter gene, the production of luciferase is indicative of receptor-regulated gene transcription.) Finally, when a ligand(s) is found that can induce transcription of the reporter gene, it is concluded that this ligand(s) can bind to the receptor protein coded for by the initial sample DNA sequence. This conclusion can be further verified by testing the binding properties of the receptor protein, coded for by the initial sample DNA sequences, vis-,1-vis the ligand(s) that induce expression of the reporter gene.

As those skilled in the art will appreciate, if a cell already contains (a) a chimeric DNA sequence (C) comprised of (1) operative portions of a DNA-binding domain of a first receptor sequence (i.e., a first sequence) linked to (2) operative portions of a ligand-binding domain of a second receptor sequence (i.e., a second sequence), and (b) a reporter nucleic acid sequence functionally linked to an operative hormone response element wherein the operative portions of the DNA-binding domain of the first receptor sequence can functionally bind to and activate the hormone response element that is functionally linked to the reporter sequence, then the method for identifying a functional ligand for a receptor protein will be comprised of challenging the cell with at least one candidate ligand and then monitoring induction of the reporter sequence by means of changes in the amount of expression product of the reporter sequence.

The new functional ligand identification assay makes it possible to screen a large number of potential ligands or any given receptors, regardless of whether the receptor is a wild-type receptor or a chimeric one.

The functional ligand identification method is illustrated herein by showing (1) that the retinoid, retinoic acid and its metabolic precurser, retinol, are functional ligands for the receptor protein coded for by phRAR1 DNA, and (2) that the DNA- and ligand-binding domains determine the functional characteristics of the chimeric receptors.

The new functional assay, as well as the new retinoic acid receptor and the new chimeric receptors, are described more fully below.

DESCRIPTION OF THE INVENTION

The Retinoic Acid Receptor

In a continuing effort to explore the steroid hormone receptor superfamily, advantage was taken of the fortuitous identification of a novel genomic sequence with striking homology to the DNA-binding domain of the steroid hormone receptors (see Dejean et al., 1986). This sequence spans the integration site of a hepatitis B virus (HBV) from a human hepatocellular carcinoma.

To pursue the hypothesis that this gene might code for a previously unknown receptor, an oligonucleotide derived from this sequence was labeled and used to probe a number of human CDNA libraries. Five positive clones were initially isolated from a testis CDNA library. The insert from one of these clones (1hT1R) was used to isolate additional CDNA clones from a λgt10 kidney CDNA library. A restriction map of the largest clone (phRAR1) is shown in FIG. 1A. Nucleotide sequence analysis reveals a long open reading frame of 462 amino acids beginning with a presumptive initiator methionine codon corresponding to nucleotides 103-105 as shown in FIG. 1B-1. The sequence surrounding this ATG agrees with the consensus described by Kozak (1987) for a translation initiation site. Upstream of the ATG is an in-frame terminator providing support for the initiator methionine. Another methionine found 30 codons downstream fails to conform to the consensus and is an unlikely initiator. Following the terminator codon at position 1489-1491 is a 3'-untranslated region with a consensus polyadenylation signal (AATAAA) found 20 nucleotides upstream of a polyadenylated tract (see Proudfoot, et al., 1976).

A polypeptide of relative molecular mass 50,772 d (51 Kd) is encoded within the translational open reading frame. The size of the protein encoded by the insert of phRAR1 was verified by in vitro translation of RNA (see Krieg, et al., (1984)) derived from this insert and found to correspond to the predicted size of 54 Kd (data not shown). Amino acid sequence of this protein has been compared to the glucocorticoid and thyroid hormone receptors. The highest degree of similarity is found in a cysteine-rich sequence of 66 amino acids beginning at residue 88. Our group has previously demonstrated that this region of the hGR represents the DNA-binding domain for this receptor. See Giguere, et al., (1987) and Hollenberg, et al., (1987). In addition, mutagenesis and expression studies have provided direct evidence for its role in transcriptional activation of genes harboring glucocorticoid response elements (GREs). See Giguere, et al , (1987) and Hollenberg, et al., (1987).

Domain Switching and Transcriptional Activation

Figure 2A:
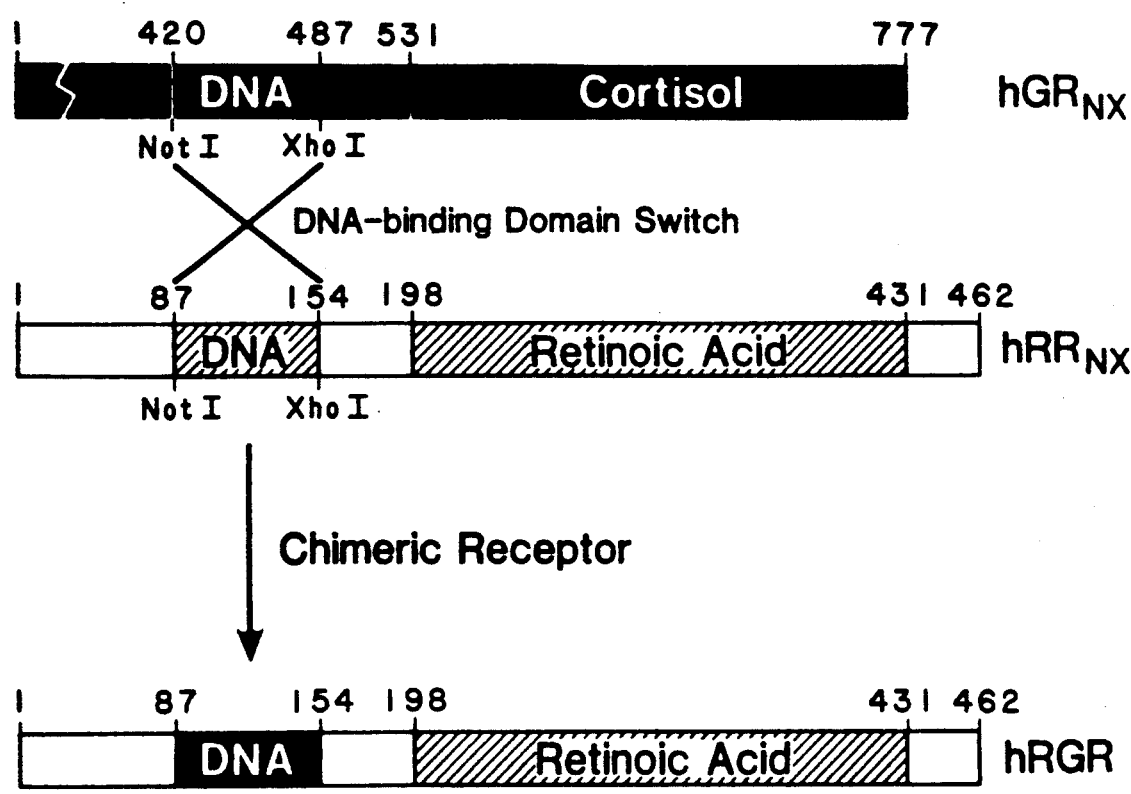
FIG. 2A is a drawing which illustrates construction of the chimeric receptor hRGR.

Since the ligand for the gene product of phRAR1 was unknown, it was desirable to develop a quick and sensitive assay to reveal its identity. Previous studies have demonstrated that the DNA-binding domain of the human glucocorticoid and estrogen receptors can be interchanged to yield a functional hybrid receptor. This chimera recognizes the glucocorticoid responsive element of the MMTV-LTR but stimulates transcription in an estrogen-dependent fashion (see Green, et al., (1987)). This led us to wonder if a general domain-swapping strategy could be exploited to identify the ligand-binding properties of a novel hormone receptor. To test this approach we first substituted the DNA-binding domain of the phRAR1 gene product with the well described DNA-binding domain from the hGR (FIG. 2A). (This chimeric construction, when expressed in suitable host cells, produces a hybrid receptor protein whose ligand-binding domain region must bind with a functional exogenous ligand before the ligand/receptor complex can bind to a GRE, thereby activating a glucocorticoid inducible promoter.)

To assay for the presence of a functional ligand the chimeric receptor gene was transfected into suitable host cells along with a suitable GRE linked reporter gene. CV-1 cells were used for the assay along with a MMTV-CAT reporter gene. (MMTV-CAT is carried on reporter plasmid, GM-CAT, which has been deposited with the American Type Culture Collection for patent purposes; see the section of this specification labeled, "Deposits". As those skilled in the art will appreciate, reporter plasmids suitable for assaying hybrid thyroid receptor proteins, i.e., hybrid proteins having the DNA-binding domain of a thyroid receptor protein, can be constructed by substituting the GRE on plasmid GM-CAT with a thyroid hormone responsive transcription element. For example, the growth hormone promoter can be functionally linked to the bacterial CAT gene. Since the growth hormone promoter contains a thyroid responsive transcription element, such a reporter plasmid can be used to assay hybrid thyroid receptor proteins. See the subheading: "Construction of Reporter and Expression Plasmids" in this specification. (Since mineralocorticoid receptors can activate GRE's, a reporter plasmid such as GM-CAT can be used to assay hybrid mineralocorticoid receptor proteins.)

Returning to the functional ligand identification assay, the transfected cells were then systematically challenged with a battery of candidate ligands and induction monitored by changes in CAT activity.

Figure 2B:
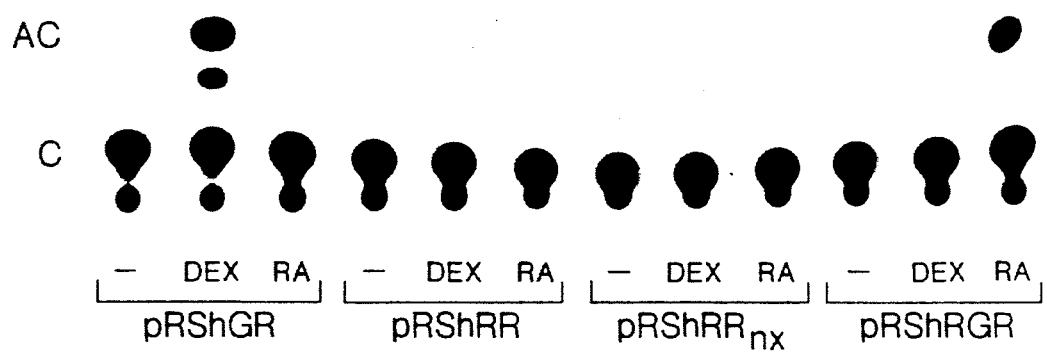
FIG. 2B is a blot which illustrates induction of CAT activity by retinoic acid.

Because of their hormonal-like activities, the retinoids, including retinol (Vitamin A) and retinoic acid, were evaluated as potential inducers. Remarkably, retinoic acid elicited a dramatic increase in CAT activity of the hybrid receptor (FIG. 2B). No effect upon CAT activity was observed using the parent vector, pRShRR$_{NX}$, or the wild type gene product from phRAR1, herein referred to as human retinoic acid receptor (hRARα). As expected, the hybrid receptor is not induced by glucocorticoids, and the hGR is not induced by retinoic acid.

As shown in FIG. 3A, retinoic acid exhibits an ED$_{50}$ value of $6 \times 10^{-10}$ M on CAT activity induced by the hybrid receptor, which is consistent with ED$_{50}$ values observed for retinoic acid in a variety of biological assays (see Sporn and Roberts, 1984). Retinol functions as a weak agonist with an ED$_{50}$ value greater than 100 rim. Retinyl acetate and retinyl palmitate function as even weaker inducers. A number of natural and synthetic ligands including testosterone, dihydrotestosterone, estrogen, dexamethasone, cortisol, aldosterone, progesterone, T$_3$, T$_4$, Vitamin D$_3$ and 25-OH-cholesterol failed to induce CAT activity.

To corroborate the identity of the phRAR1 gene product as the retinoic acid receptor, the binding properties of the expressed product were evaluated following transfection of COS-1 cells. As shown in FIG. 3B, transfected cells reveal increased capacity to specifically bind $^3$H-retinoic acid. This increase occurs over an endogenous background that is a likely consequence of the presence of cellular retinoid binding proteins as well as a significant nonspecific binding. Consistent with the activation studies, the binding is fully competed by retinoic acid but only partially by retinol. Thyroid hormones, dexamethasone and vitamin $D_3$ did not compete the binding of retinoic acid.

A Gene Family

Figure 4A:
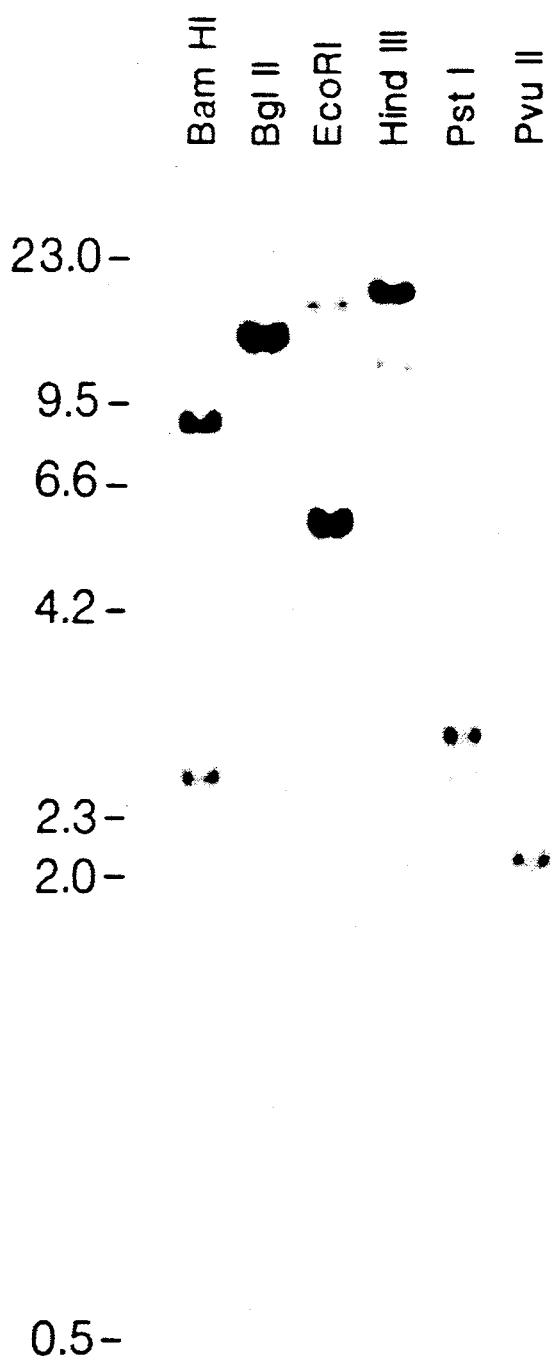
FIG. 4A shows digested human placenta DNA hybridized under stringent conditions.
Figure 4B:
FIG. 4B shows the same DNA hybridized under nonstringent conditions.

To determine if the new retinoic acid gene was unique and to identify potentially related genes, human DNA was examined by Southern blot analysis. Hybridization of restriction endonuclease-digested human DNA with a labeled DNA fragment derived from the coding region of the hRR gene produced three bands in every digestion consistent with a single hybridizing genetic locus (FIG. 4A). This hybridization pattern is unrelated to the restriction endonuclease map described by Dejean et al. (1986) for the HBV preintegration site. However, when the hybridization conditions were relaxed, six additional bands were observed in the products of each enzyme digestion (FIG. 4B). These observations suggested that there were at least one additional locus, and possibly more, in the human genome related to the retinoic acid receptor. The RAR$\beta$ has now been found. See Brand, et al, (1988).

Expression of the hRR Gene

Since retinoic acid is known to exert effects on a large number of different cell types, we examined the expression of the hRR gene. Total cytoplasmic RNAs isolated from a variety of rat and human tissues were size fractionated and transferred to a nitrocellulose filter. Hybridization with a 600-bp restriction fragment from phRAR1 reveals a major RNA species of 3,200 nucleotides with highest levels in the hippocampus, adrenals, cerebellum, hypothalamus and testis (FIG. 5). Longer exposure shows that most tissues contain a small amount of the 3.2 kb transcript while it is undetectable in some tissues such as liver.

Retinoic Acid Receptor Data Summary

The data disclosed herein identify the gene product of phRAR1 as a human retinoic acid receptor based on three criteria. First, the overall structural homology of the hRR to steroid and thyroid hormone receptors (FIG. 6) suggests that it is likely to be a ligand-responsive regulatory protein. Second, an expressed chimeric receptor, consisting of the DNA-binding domain of the hGR and the presumptive ligand-binding domain of the hRR acts as a transcriptional regulator of a glucocorticoid-inducible reporter gene only in the presence of retinoic acid. This induction occurs at physiological levels. Third, expression of the candidate hRR in transfected cells selectively increases the capacity of those cells to bind retinoic acid.

Development and Oncogenesis

The retinoids comprise a group of compounds including retinoic acid, retinol (vitamin A) and a series of natural and synthetic derivatives that together exert profound effects on development and differentiation in a wide variety of systems. See Sporn & Roberts, (1983); Mandel & Cohen, (1985); Wolback & Howe, (1925); Lotan (1980); and Fuchs & Green, (1980). Although early studies focused on the effects of retinoids on epithelial growth and differentiation, their actions have been shown to be more widespread than previously suspected. Many recent studies demonstrate the effects of these molecules on a variety of cultured cell lines including neuroblastomas (see Hausler, et al., (1983) melanomas (see Lotan, et al., (1983) ) and fibroblasts (see Shroder et al., (1982)). In the human promyelocytic leukemia cells (HL-60), retinoic acid is a potent inducer of granulocyte differentiation (see Breitman, et al., (1980)). In F9 teracarcinoma stem cells, retinoic acid will induce the differentiation of parietal endoderm, characteristic of a late mouse blastocyst (see Strickland & Mahdavi, (1978); Jetten et al., (1979); and Wang et al., (1985)). Retinoic acid has been shown to exert equally potent effects in development. For example, in the developing chick limb bud, retinoic acid is able to substitute for the action of the polarizing region in establishing the anterior-posterior axis (see Tickle & Eichele, (1985)). By controlling the exposure to retinoic acid, it is possible to generate novel patterns of limb structures. Although retinoic acid is primarily considered a morphogen, Northern blot analysis suggests a re-evaluation of its function in the adult. In humans, retinol deficiency has been linked to an alarming increase in a variety of cancers (see Moon & Itri, (1984)). Retinoids have also been shown to inhibit tumor progression in animals and block the action of tumor promoters in vitro. In this context, the hRR may be considered as a negative regulator of oncogenesis.

A Superfamily of Regulatory Genes

Two surprising results have emerged from the studies presented here. The first is the discovery of a family of retinoic acid receptor-related genes which predicts the existence of one or more other proteins with closely related properties (e.g., the RAR$\beta$ described by Brand et al, (1988)). Physiological studies demonstrate that both retinoic acid as well as retinol (vitamin A) can exert potent effects on cellular differentiation and that these effects are often not linked. It thus seems likely that at least one related gene product might be a specific retinol receptor or a receptor for another member of the retinoid family. The second surprising observation from these results is the close kinship of the retinoid receptor with the thyroid hormone receptor. (As we show below, the retinoic acid receptor can activate a thyroid response element or TRE; see the section of the specification labeled "Retinoic Acid and Thyroid Hormone Induce Gene Expression Through a Common Response Element".) This relationship is surprising in part because of the structural dissimilarity of the thyroid hormones and the retinoids. Thyroid hormones being derived from the condensation of two tyrosine molecules whereas, the retinoids are derived from mevalonic acid. The observation that chemically distinct molecules interact with receptors sharing common structures most likely reflects a common mode of action with which they elicit their particular regulatory effects. Based on this analogy, we can now propose that the interaction of retinoids with their intracellular receptors induces a cascade of regulatory events that results from the activation of specific sets of genes by the hormone/receptor complex. Although animals employ diverse means to control their development and physiology, the demonstration that the retinoic acid receptor is part of the steroid receptor superfamily suggests that mechanisms controlling morphogenesis and homeostasis may be more universal than previously suspected.

Construction and Characterization of Chimeric Receptors

Construction of chimeric receptor genes is discussed above in the sections of the specification labeled "Definitions", "Summary of the Invention" and "Domain Switching and Transcriptional Activation". In the sections that follow, construction and characterization of the chimeric receptors is illustrated by showing construction and and characterization of GR/TR hybrids.

Materials and Methods Cell Culture and Transfection

CV-1 cells were used as the receptor-deficient host cells that were transfected with expression plasmids that carry the chimeric RR/TR receptors, and reporter plasmids carrying the CAT reporter gene. Conditions for growth and transfection of CV-1 (African Green monkey kidney) cells were as previously described (Giguere et al. (1986), except that the calcium phosphate precipitate was left on the cells for 4-8 hours, at which time the media was changed to DMEM with 5% $T_3$ free bovine serum (Scantibodies) minus or plus $10^{-7}$ M $T_3$ (Sigma). Cells were harvested 36 hours after the addition of $T_3$, and CAT assays were performed as described by Gorman el al. (1982). Typically, 5 μg reporter and 1 μg expression vector were cotransfected, along with 2.5 μg RSV-βgal as a control for transfection efficiency. Acetylated and non-acetylated forms of [$^{14}$C]chloramphenicol were separated by thin layer chromatography, excised, and quantitated by liquid scintillation counting in Econofluor (DuPont) with 5% DMSO. β-galactosidase assays were performed as described by Herbomel et al. (1984). CAT activity is expressed as percent conversion divided by β-galactosidase activity.

Construction of Reporter and Expression Plasmids

Synthetic oligonucleotides corresponding to $-169$ to $-200$ of the rat growth hormone gene was inserted into a linker scanning mutant of MTV- CAT that has a HindIII site at position $-190/-181$ (Buetti and Kuhnel (1986)). Expression vectors were constructed for the thyroid hormone receptors by inserting the full-length cDNAs of pheAl2 (hTRβ, see Weinberger, et al. (1986)) and rbeAl2 (rTRα, see Thompson, et al. (1987)) between the KpnI and BamHI sites of the pRS vector (Giguere, et al. (1986) and (1987)

Construction of Chimeric Receptors

The construction of hGR$_{NX}$ has been described (Giguere, et al. (1987) To construct hTRβ$_{NX}$, the CDNA insert of pheAl2 (HTRβ, see, Weinberger, el al. (1985) and (1986)) was subcloned between the KpmI and BamHI sites of M13MP19 and mutagenized by the method of Kunkel (1985). The oligonucleotide used to create the NotI site changed three amino acids: Asp97 to Arg, Lys98 to Pro, Asp99 to Pro. The oligonucleotide used to create the XhoI site changed two amino acids: Thr171 to Leu, Asp172 to Gly. The mutant receptor CDNA was then transferred to the expression vector pRS (Giguere, et al. (1986) and (1987) ) ; hybrids were constructed by exchanging KpnI-NotI, KptiI-XhoI, or NotI-XhoI restriction fragments between RShGR$_{NX}$ and RShTPβ$_{NX}$. RShGR$_{NX}$ has about 75% of wild-type DNA-binding activity, and RShTPβ$_{NX}$ has about 60% of wild-type DNA-binding activity.

The Cis/Trans Functional Ligand Identification Assay

The cis/trans functional ligand identification cotransfection assay was used to study chimeric receptors constructed by swapping domains between the glucocorticlod, the thyroid and the retinoic acid receptors. (As those skilled in the art will appreciate, the cis/trans cotransfection assay can be used to study chimeric receptors made by swapping functional between any of the wild-type or genetically engineered receptors.) In the cis/trans assay, preferably two plasmids are transfected into a receptor deficient cell line. The first plasmid is used to express the receptor protein (whether wild-type, chimeric or genetically engineered). The second plasmid is used to monitor transcription from a ligand or hormone responsive promoter. For the thyroid hormone receptor assay, the expression plasmid consists of the Rous Sarcoma Virus long terminal repeat (RSV-LTR) directing the expression of a cDNA encoding a thyroid hormone receptor. For the hGR, the reporter plasmid is the mouse mammary tumor virus long terminal repeat (MTV-LTR) fused to the bacterial chloramphenicol acetyltransferase (CAT) gene. To convert MTV-CAT to a thyroid hormone responsive reporter, an oligonucleotide containing a thyroid hormone response element (TRE) was inserted at position $-191$ of the MTV-LTR. This sequence, $-169$ to $-200$ of the rat growth hormone (rGH) gene, specifically binds thyroid hormone receptors and can confer $T_3$ responsiveness to a heterologous promoter (Glass el al. (1987)). Expression and reporter plasmids were cotransfected into CV-1 cells and CAT activity was measured in the absence and presence of $T_3$. The assays showed that neither the alpha nor the beta thyroid hormone receptor activates transcription from MTV- CAT, in the absence or presence of $T_3$. (Data not shown.) However, the addition of a TRE produces an MTV promoter that is thyroid hormone responsive. Induction of CAT activity is dependent on the cotransfection of a functional alpha or beta thyroid hormone receptor and the addition of $T_3$. In the presence of $T_3$, the alpha receptor (rTRα) induces CAT activity approximately 15-fold, while the beta receptor (hTPβ) induces activity by about 5-fold.

The hybrid thyroid hormone/glucocorticoid receptors were constructed to compare the functional properties of the thyroid and glucocorticoid hormone receptors. To facilitate the construction of the chimeric hybrid receptors, unique sites for the restriction enzymes NotI and XhoI were inserted flanking the DNA binding domains of hGR and HTPβ. These mutant receptors, termed hGR$_{NX}$ and hTPβ$_{NX}$, can be used to create hybrids with all possible combinations of amino termini, DNA-binding domains, and ligand-binding domains for these receptors. (As those skilled in the art will appreciate, comparable plasmids, such as pRARα$_{NX}$ or pMR$_{NX}$ for example, can be used to create chimeric receptors consisting of all possible combinations of all functional domains from the various receptors in the steroid hormone receptor superfamily. The receptors and the locations of the various functional domains are shown in FIG. 8-1). The hybrid and parental receptors were assayed using both thyroid hormone and glucocorticoid responsive promoters, in the absence or presence of Thd 3 or the synthetic glucocorticoid dexamethasone.

Figure 9:
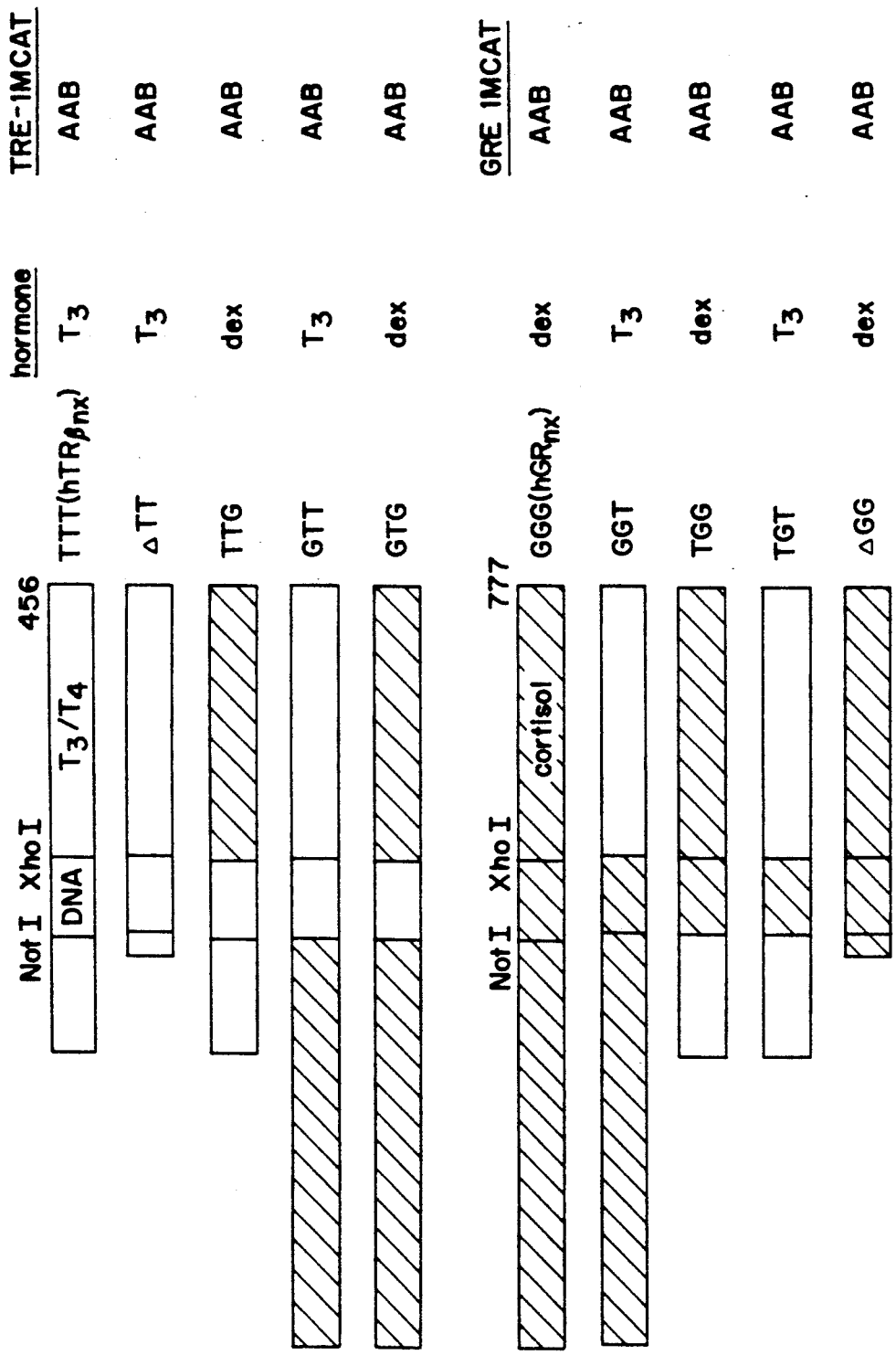
FIG. 9 is a schematic drawing that shows the structure and activity of chimeric thyroid/glucocorticoid receptors.

The structures and activities of the hybrid thyroid/glucocorticoid receptors are shown in FIG. 9. The receptors are divided into three sections, and hybrids are named by letters referring to the "origin" of the domain; for example, "T-G-T" has the amino and carboxyl termini of hTPβ (T-,-T) and the DNA binding domain of the hGR (-G-). Hybrids with a putative hTRβ DNA binding domain (TTG, GTT, GTG) activated transcription from TRE- CAT, while hybrids with an hGR DNA binding domain (GGT, TGG, TGT) activated transcription from GRE- CAT. This demonstrates that this region of htpβ is analogous to the hGR DNA binding domain and is responsible for promoter recognition. Hybrid receptors with an hTPβ carboxyl terminus were activated by $T_3$, while those with an hGR carboxyl terminus were activated by dexamethasone. This is consistent with the identification of the carboxyl terminus as the part of the receptor that is responsible for hormone binding and activation specificity. Taken together, the functional properties of these hybrids support the assignment of the DNA- and ligand-binding domains of hTRβ.

Retinoic Acid and Thyroid Hormone Induce Gene Expression Through a Common Responsive Element Identification of a functional retinoic acid responsive element (RARE) is crucial to our understanding of the mechanisms by which retinoic acid receptors activate gene expression and regulate cell differentiation. One impediment to such a study is the absence of any identified gene whose transcription is directly dependent on the retinoic acid receptor-hormone complex. An alternative approach to localize a RARE is to systematically challenge the inducibility of known hormonally responsive promoters with retinoic acid receptor produced from cloned cDNA. (As discussed above under the heading "The Cis/Trans Assay", in this system, transcriptional activation from a promoter containing a HRE is dependent on expression of functional receptor from cotransfected expression plasmids in receptorless cells such as CV-1.) Because the DNA-binding domains of the retinoic acid and thyroid hormone receptors are highly related (62% identical in their amino acid sequences, see FIG. 6), the possibility that the retinoic acid receptor could activate gene expression through a TRE was investigated.

TRE's are known; see, or example, Glass, et al, (1987) for a discussion of a cis-acting element in the rat growth hormone 5' flanking genomic sequence that is necessary for thyroid hormone (3,5,3'-triiodo-L-thyronine, $T_3$) regulation.

To test if a TRE could effectively function as a RARE, a novel $T_3$ responsive promoter was constructed by replacing the glucocorticoid responsive elements present in the mouse Mammary Tumour Virus-Long Terminal Repeat (MTV-LTR) with an oligonucleotide encoding the natural $TRE_{GH}$. This promoter was then fused to the bacterial chloramphenicol acetyl transferase (CAT) gene to generate the reporter plasmid ΔMTV-$TRE_{GH}$-CAT. After transient transfection into CV-1 cells, the inducibility of the promoter was determined by measuring CAT activity. When CV-1 cells are cotransfectd with the expression vector containing a human thyroid hormone receptor beta (pRShT₃Rβ) and the reporter plasmid ΔMTV-$TRE_{GH}$-CAT, induction in CAT activity is observed in the presence of $T_3$. In contrast, cotransfection of an expression vector encoding the human glucocorticoid receptor (pRShGRα) and the same reporter plasmid did not stimulate CAT activity from this promoter in response to the synthetic glucocorticoid dexamethasone. These results clearly demonstrate that the induction of CAT activity by RARα is conferred by the TRE because the wild-type MTV-LTR construct was not responsive. (Data not shown.) These results also show that the hRARα can specifically induce gene expression from a promoter containing a TRE.

RAR and GR Chimeric Receptors

As discussed above, the modular structure of steroid hormone receptors makes it possible to exchange functional domains from one receptor to another to create functional chimeric receptors. This strategy was used to create hGR/hRARα chimera that had the RAR DNA-binding domain and the GR ligand-binding domain. When CV-1 cells were cotransfected with the expression plasmid encoding hGRG and the reporter ΔMTV-$TRE_{GH}$-CAT, dexamethasone specifically elicited CAT activity. (Data not shown.) This experiment provided direct evidence that the DNA-binding domain of the hRARα determined the specificity of target gene activation.

DETAILED DESCRIPTION OF THE DRAWINGS

FIG. 1. DNA and primary amino acid sequence of phRAR1. A, Schematic representation and restriction enzyme map of the phRAR1 clone. The stippled box represents the predicted open reading frame. B, (shown as B-1, and B-2. The complete nucleotide sequence of phRAR1 is shown with the amino acid sequence given above the long open reading frame. An upstream in-frame stop codon at nucleotides 85-87 and polyadenylation signal are underlined.

FIG. 1 Methods. A 63-mer oligonucleotide corresponding to nucleotides 408-477 of the genomic sequence published by Dejean et al. (1986) was used as a hybridization probe to screen a human testis λgt10 library. The hybridization mixture contained 35% formamide, 1X Denhardt's, 5X SSPE, 0.1% sodium dodecyl sulfate (SDS), 100 μg ml$^{-1}$denaturated salmon sperm DNA and $10^6$ c.p.m. ml$^{-1}$ of $^{32}$p-labeled oligonucleotide. Duplicate nitrocellulose filters were hybridized at 42° C. for 16 h, washed three times for 20 min each in 2X SSC, 0.1% SDS (LXSSC=150 Mm NaCl, 15 Mm sodium citrate) at 55° C. and autoradiographed at −70° C. with an intensifying screen. Clone 1hT1R obtained from this screening was partially characterized and then used as a hybridizing probe to screen a human kidney λgt10 library (see Bell, et al., (1986)). For this screening, the washing conditions were modified to 1XSSC with 0.1% SDS at 68° C. Several cDNA clones were isolated and the longest clone, phRAR1, was digested with a number of restriction enzymes and the resulting fragments were subcloned in both orientations into the M13 sequencing vectors mp18 and mp19 and sequenced by the dideoxy procedure (see Sanger, el al., (1977)). DNA sequences were compiled and analyzed by the programs of Devereux el al. (1984) and Staden (1982).

FIG. 2. A, Construction of the chimeric receptor HRGR. The domain-structure of the various constructions are shown schematically, the numbers correspond to the amino acid positions of each domain. The DNA-binding domains are represented by "DNA" and the ligand-binding domains by their respective inducers. The NotI and XhoI sites created by site-directed mutagenesis to permit the exchange of the DNA-binding domains between receptors are indicated. B, Induction of CAT activity by retinoic acid. The expression vectors were cotransfected into CV-1 cells with the reporter plasmid MTVCAT and cultured for 2 days in absence or presence of 100 nM dexamethasone (DEX) or retinoic acid (RA). The receptor inserted into the expression vectors are: pRShGR, human glucocorticoid receptor; pRShRR, human retinoic acid receptor; pRShRR$_{nx}$, mutated human retinoic acid receptor with NotI and XhoI sites; pRShRGR, chimeric receptor composed of the human retinoic acid receptor which DNA-binding domain has been replaced by the human glucocorticoid receptor DNA-binding domain.

FIG. 2 Methods. A, Restriction enzyme fragments of the CDNA inserts of phRAR1 and hGR (see Hollenberg, et al., (1985) were subcloned into the Kpn1 and BomH1 sites of the mp19 vector and mutagenized according to the method of Kunkel (1985). The oligonucleotides used for the creation of the NoII site within hGR and hRR were 28 and 31 nucleotides respectively, while the oligonucleotides used for the creation of the XhoI site within hGR and hRR were 24 and 23 nucleotides. The creation of the NotI site resulted in the mutation of Pro$_{416}$ to an Arg residue in hGR$_{NX}$, and in the mutation of Ile$_{48}$ and Tyr$_{85}$ to Pro residues in HRR$_{NX}$. The introduction of the XhoI site did not alter the HGR$_{NX}$ amino acid sequence but resulted in the mutation of Lys$_{155}$ to a Leu residue in HRR$_{NX}$. The mutant receptors were then transferred to the expression vector pRS (see Giguere, eial., (1986), and the Not1/Xhol restriction fragment of pRShGR$_{NX}$ containing the hGR DNA-binding domain was introduced into pRShRnx between the NotI and XhoI sites to create pRShRGR. B, Cell transfection and CAT assay. The recombinant DNA constructs (5 µg each) were introduced into CV-1 cells by calcium phosphate coprecipitation (see Wigler, el al., (1979)). The cells were then cultured for two days in serum free media supplemented with Nutridoma (Boehringer Mannheim) in presence or absence of inducers. CV-1 cells were then prepared for CAT assays as described by Gorman, et al. (1982) and the assays performed for 3 h using 25 µg of protein extract. All experiments with retinol were conducted in subdued light.

FIG. 3. A, Dose-response to retinoids. CV-1 cells cotransfected with pRShRGR and PMTVCAT were treated with increasing concentrations of retinoids or a single 1 µM dose (*) of testosterone, dihydrotestosterone, estrogen, cortisol, aldosterone, progesterone, triiodothyronine (T$_3$), thyroxine (T$_4$), dihydroxy-vitamin D$_3$ (VD$_3$) and 25-OH-cholesterol. The levels of CAT activity were plotted as percentages of the maximal response observed in this experiment. B, Retinoic acid binding to cytosol extracts of transfected COS-1 cells. Bars represent bound $^3$H-retinoic acid determined in absence (black bars) or presence (stippled bars) of a 1000-fold excess of various competitors. The values represent the mean of quadruplicate determinations. Competitors are retinoic acid (RA), retinol (R), T$_4$, dexamethasone (DEX) and vitamin D$_3$ (VD$_3$).

FIG. 3 Methods. A, CV-1 cell cotransfections and CAT assays were performed as described in FIG. 2. Retinoic acid was dissolved in a minimum volume of dimethyl sulfoxide and diluted in ethanol. All other products were diluted in ethanol and control cultures received 0.1% solvent (v/v) in media. Dose-response curves of retinoid treatment were performed in triplicate. B, Subconfluent COS-1 cells were transfected with 10 µg/dish of a control plasmid (pRS) or pRShRR by the DEAE-Dextran method (see Deans, etal., (1984)). Cells were maintained for 2 days in DMEM with 5% charcoal-treated fetal calf serum, then harvested in TNE (40 mM tris-HCl pH 7.5, 150 Mm NaCl, 1 mM EDTA) and lysed by Dounce homogenization in hypotonic buffer (50 Mm tris-HCl pH 7.4, 0.1 Mm EDTA, 5 mM dithiothreitol, 10 mM NaMoO$_4$, 10% glycerol, 0.5 mM phenylmethylsulfonyl fluoride) and centrifuged at 100,000 ×g for 30 min to yield the cytosol fraction. Incubations were performed in hypotonic buffer with 150 µg of protein from the cytosolic fraction and $2\times10^{-8}$ M $^3$H-retinoic acid (NEN, 52.5 Ci/mmole) in a total volume of 200 µl. Specific binding was measured by the addition of $2\times10^{-5}$ M of competitors. Reactions were carried out at 40° C. for 16 h. Bound $^3$H-retinoic acid was quantitated using DE-81 filters. Reactions were placed on filters for 1 min and then rinsed with 5 ml of washing buffer (50 mM tris-HCl pH 7.4, 0.1 mM EDTA, 0.1% Triton X-100). Filters were dried and counted by liquid scintillation spectrophotometry.

FIG. 4. Southern blot analysis of human genomic DNA. A, Human placenta DNA was digested with the indicated restriction enzymes. After separation of the digested DNA in a 0.8% agarose gel (10 µg/lane) and transfer to nitrocellulose filters (see Southern, (1975), the blots were hybridized with an EcoRl X PvuII fragment from phRAR1 (~600 bp) encompassing the DNA-binding domain of the hRR under high stringency conditions (50% formamide, 5X SSPE, 1X Denhardt's, 0.1% SDS, 100 pg ml$^{-1}$ salmon sperm DNA). The filter was washed in 0.1X SSC, 0.1% SDS at 65° C. Lambda HindIII DNA markers (size in Kb) are aligned to left of the autoradiogram. B, Analysis of human placenta DNA using the same probe as in A under non-stringent conditions. A parallel blot containing identical samples was hybridized as in A, except that 35% formamide was used. The filter was washed in 2XSSC, 0.1% SDS at 55° C.

FIG. 5. Northern blot analysis of retinoic acid receptor MRNA in rat and human tissues.

FIG. 5 Methods. Total RNA was isolated from various tissues using guanidine thyocyanate (see Chirgwin, et al., (1980), separated on 1% agarose-formaldehyde gel, transferred to nitrocellulose, and hybridized under stringent conditions using the probe described in FIG. 4. Twenty µg of total RNA was used in all lanes. Migration of ribosomal RNA's (28S and 18S) are indicated for size markers. The nitrocellulose filter was autoradiographed at −70° C. with an intensifying screen for 1 week.

Figure 6:
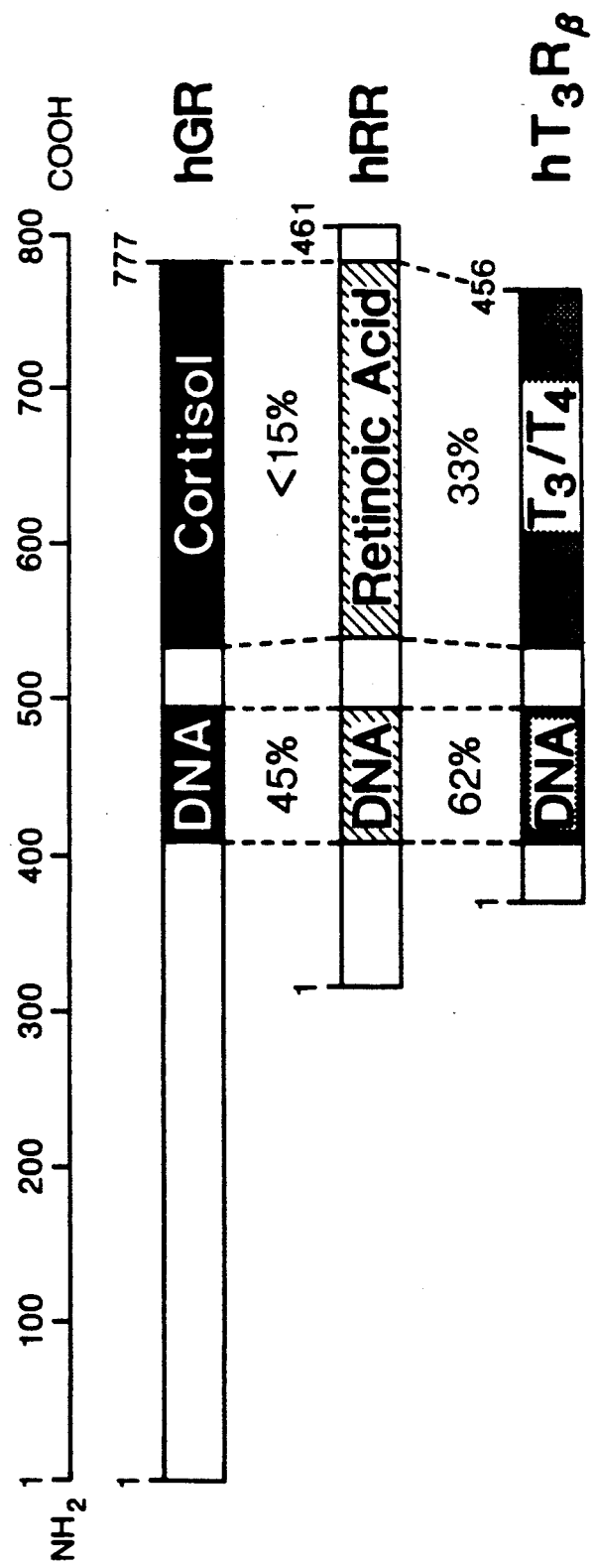
FIG. 6 is a schematic drawing which shows a comparison of hGR, hRR and hT$_3$Pβ.

FIG. 6. Schematic amino acid comparisons of the hGR, hRR and hT$_3$P$\beta$ structures. Amino acid sequences have been aligned schematically with the percentage amino acid identity for each region of homology in the intervals between dotted lines.

Figure 7:
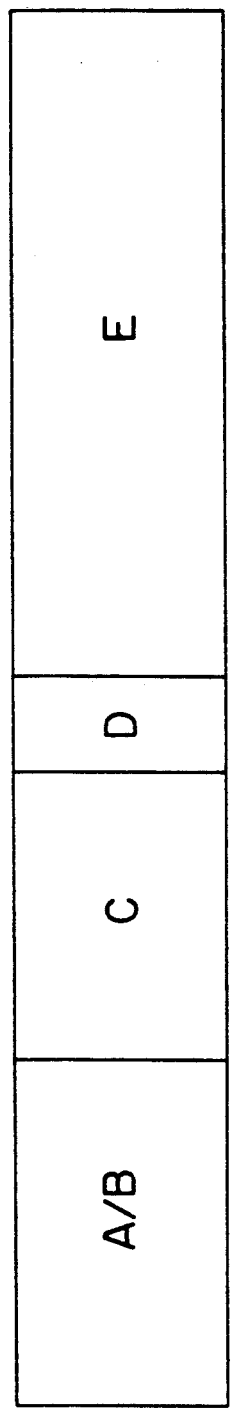
FIG. 7 is a schematic diagram of a generalized steroid/thyroid/retinoic acid receptor gene.

FIG. 7 is a schematic diagram of a generalized steroid/thyroid/retinoic acid receptor gene, showing the division of the gene into regions A/B, C, D, and E. The function of the A/B region is just beginning to be elucidated; the C region encodes the DNA-binding domain; the D region is believed to be a hinge region; and the E region encodes the ligand-binding domain.

FIG. 8(1 and 2) is a schematic drawing that shows amino acid comparison of members of the steroid hormone receptor superfamily. Primary amino acid sequences have been aligned on the basis of regions of maximum amino acid similarity, with the percentage amino acid identity indicated for each region in relation to the hGR (Miller et al., (1985). Domains shown are: a domain at the $NH_2$-terminal end that is required for "maximum activity"; the 66- to 68-amino acid DNA-binding domain core ("DNA"); and the 250-amino acid ligand-binding (or hormone-binding domain) ("Hormone"). The amino acid position of each domain boundary is shown. Amino acid numbers for all receptors represent the human forms with the exception of V-erb-A and E75 (Segraves, 1988). Functional assignments have been determined by characterization of the glucocorticoid and estrogen receptors. Designations are as follows: GR, glucocorticoid receptor; MR mineralocorticoid receptor; PR, progesterone receptor; ER, estrogen receptor; ERR1 or ERR2, estrogen-related 1 or 2; VDR, vitamin $D_3$ receptor; and $T_3R\beta$ and $T_3R_\alpha$, thyroid hormone receptors. The (+) or (−) indicates whether a particular property has been demonstrated for the products of cloned receptor cDNA or with purified receptor. HRE, hormone response element. This relates to whether the binding site has been identified structurally and whether its enhancement properties have been demonstrated by gene transfer studies. For PR, DNA-binding properties have been shown only with the native purified receptor. "Hormone binding in vitro" indicates whether this property has been demonstrated by translation in a rabbit reticulocyte lysate system (Hollenberg eial, 1985). "Hormone binding in vivo" refers to expression of the cloned receptor in transfected cells. "Chromosome" indicates the human chromosome location. Species are as follows: h, human; r, rat; m, mouse; c, chicken; and d, Drosophilia.

FIG. 9. Structure and activity of chimeric thyroid-/glucocorticoid receptors.

FIG. 9 Methods. To construct hybrid receptors, unique NotI and XhoI sites were inserted flanking the DNA binding domains of the hGR and $HTP\beta$. Hybrids were created by exchanging the appropriate segments of the receptor cDNA's. "DNA" indicates the DNA binding domain; "$T_3/T_4$" and "cortisol" indicate the ligand binding domains of $HTP\beta$ and hGR respectively. The numbers above the boxes indicate amino acid residues. Hybrids are named by letters referring to the origin of the domain; for example, "TGT" has the amino and carboxyl termini of $hTP\beta$ and the DNA binding domain of the hGR. All receptors were assayed on TRE-MCAT and GRE-MCAT in the absence and presence of $T_3$ and the synthetic glucocorticoid dexamethasone ("dex"). All of the combinations shown gave activation above background.

REFERENCES

The present specification refers to the following publications, each of which is expressly incorporated by reference herein.
1. Arriza, J., et al., *Science* 237:268-275 (1987).
2. Bell, G. I., et al., *Nucleic Acid Res.* 14:8427-8446 (1986).
3. Breitman, T., Selonick, S. & Collins, S. J., *Proc. Natl. Acad. Sci., USA* 77:2936-2940 (1980).
4. Buetti, E. and Kuhnel, B., *J. Molec. Biol.* 190:379-389 (1986).
5. Chirgwin, J. M, Przybyla, A. F., McDonald, R. J. & Rutter, W. F., *Biochemistry* 18:5294-5299 (1980).
6. Colantuoni, V., Cortese, R., Nilsson, M., Lundvall, J., Bavik, C., Eriksson, U., Peterson, P. A. & Sundel, J. *Biochem. Biophys. Res. Commun.* 130:431-439 (1985).
7. Deans, R. J., el al., *Proc. Natl. Acad. Sci., USA* 81:1292-1296 (1984).
8. Dejean, A., Bougueleret, L., Grzeschik, K.-H. & Tiollais, P., *Nature* 322:70-72 (1986).
9. Devereux, J., Haeberli, P. & Smithies, O., *Nucleic Acid Res.* 12:387-395 (1984).
10. Eberhardt, N. L., Apriletti, J. W., Baxter, J. B., in *Biochemical Actions of Hormones*, G. Litwack, Ed, Vol. 7, pp. 311-394, Academic Press, New York, (1980).
11. Evans, R., *Science* 240:889-895 (1988).
12. Fuchs, E. & Green, H., *Cell* 25:617-625 (1980).
13. Giguere, V., Hollenberg, S. M., Rosenfeld, M. G. & Evans, R. M., *Cell* 46:645-652 (1986).
14. Giguere, V., Ong, E. S., Segui, P., and Evans, R. M., *Nature* 330, 624-629 (1987).
15. Giguere, V., Yang, N., Segui, P., and Evans, R. M., *Nature* 331, 91- (1988).
16. Glass, C. K., Franco, R., Weinberger, C., Albert, V. R., Evans, R. M., and Rosenfeld, M. G., *Nature* 329:738-741 (1987).
17. Glass, C. K., Holloway, J. M., Devary, O. V., and Rosenfeld, M. G., *Cell* 54:313-323 (1988).
18. Gorman, C. M., Moffat, L. F. & Howard, B. H., *Mol. Cell. Biol.* 2:1044-1051 (1982).
19. Green, S. & Chambon, P., *Nature* 325:75-78 (1987).
20. Green, S., et al., *Nature* 320:134-139 (1986).
21. Hausler, M., Sidell, N., Kelly, M., Donaldson, C., Altman, A. & Hollenberg, S. M., & Mangelsdorf, D., *Proc. Natl. Acad. Sci., USA* 80:5525-5529 (1983).
22. Hollenberg, et al., *Nature* 318: 635-641 (1985).
23. Hollenberg, S. M., Giguere, V., Segui, P. & Evans, R. M., *Cell* 49:39 (1987).
24. Hollenberg S. M. and Evans, R. M., in press.
25. Izumo, S. and Mahdavi, V., *Nature* 334, 539-542 (1988).
26. Jetten, A., Jetten, M. & Sherman, M., *Exp. Cell Res.* 124:381-392 (1979).
27. Koenig, R. J., Brent, G. A., Warne, R. L., Larsen, P. R., and Moore, D. D., *Proc. Natl. Acad. Sci., USA* 84: 5670-5674 (1987)
28. Koenig, R. J., Warne, R. L., Brent, G. A., Harney, J. W., Larsen, P. R. and Moore, D. D. *Proc. Natl. Acad. Sci., USA* 85: 5031-5035 (1988).
29. Kozak, M., *Nucleic Acid Res.* 12, 857-872 (1984)
30. Kozak, M., *Nucleic Acid Res.* 16: 8125-8148 (1987).
31. Krieg, P. A. & Melton D. A., *Nucleic Acid Res.* 12:7057-7070 (1984).
32. Kumar, V., Green, S., Stark, G., Berry, M., Jin, J.-R. & Chambon, P., *Cell* 51:941-951 (1987).
33. Kunkel, T. A., *Proc. Natl. Acad. Sci., USA* 82:488-492 (1985).
34. Lotan, R., *Biochim. Biphys. Acta* 605:23-91 (1980).
35. Lotan, R., Stolarsky, T. & Lotan, D., *Cancer Res.* 43: 2868-2875 (1983).
36. Mandel, G. & Cohen, V., in *The Pharmacological Basis of Therapeutics* (eds. Gilinan, A., Goodman, L., Rall, T., Mural, F.) 1573-1591 (Macmillan, New York, 1985).
37. Mangelsdorf, D., *Proc. Natl. Acad. Sci., USA* 80:5525-5529 (1983).
38. Miesfeld, R., Godowski, P. J., Maler, B., & Yamamoto, K. R., *Science* 236:423-427 (1987).
39. Miller J., McLachlan, A., & Klug, A., *EMBO J.* 4: 1609 (1985).

40. Moon, R. C. & Itri, L. M., in *The Retinoids* (eds. Sporn, M. B. , Roberts, A. B., Goodman, D. S.) 327-371 (Academic Press, New York, 1984).
41. Munoz, A., Zenke, M., Gehring, U., Sap, J., Beug, H., and Vennstrom, B., *EMBO J.* 7, 155-159 (1988).
42. Proudfoot, N. J. & Brownlee, G. G., Nature 263:211-214 (1976).
43. Sanger, F., Nicklen, S. & Coulson, A. R., *Proc. Natl. Acad. Sci., USA* 74: 5463-5467 (1977)
44. Sap, J. Munoz, A., Damm, K., Goldberg, Y., Ghysdael, J., Leutz, A., Beug, H. & Vennstrom, B., *Nature* 324: 635-640 (1986).
45. Schwartz, H. L., in *Molecular Basis of Thyroid Hormone Action*, J. H. Oppenheimer and H. H. Samuels, Eds, pp. 413-444 Academic Press, New York, (1983).
46. Segraves, W., thesis, Stanford University, (1988).
47. Shroder, E., Rapaport, E., Kabeenell, K. & Black, P. H., *Proc. Natl. Acad. Sci., USA* 79:1549-1552 (1982).
48. Sigler, P. B., *Nature* 333: 210-212 (1988)
49. Southern, E. M., *J. Molec. Biol.* 98:503-517 (1975).
50. Sporn, M. & Roberts, A. B., *Cancer Res.* 43:3034-3040 (1983).
51. Sporn, M. B. & Roberts, A. B., in *The Retinoids*, Vol. 1 (eds. Sporn, M. B., Roberts, A. B., Goodman, D. S.) 235-279 (Academic Press, New York, 1984).
52. Strahle, U., Klock, G., and Schutz, G. *Proc. Natl. Acad. Sci., USA* 84: 7871-7875 (1987)
53. Strickland, S. & Mahdavi, V., *Cell* 15:393-403 (1978).
54. Staden, R., *Nucleic Acid Res.* 10: 2951-2961 (1982).
55. Tora, L., Gronemeyer, H., Turcotte, B., Gaub, M-P. , and Chambon, P., *Nature* 333:185-188 (1988).
56. Thompson, C. C., Weinberger, C., Lebo, R. & Evans, R. M., *Science* 237: 1610-1614 (1987).
57. Tickle, C., Lee, J. & Eichele, G., *Devel. Biol.* 109:82-95 (1985).
58. Umesono, K., Giguere, V., Glass, C., Rosenfeld, M., & Evans, R., *Nature*, 336:262-265 (1988).
59. Wang, S.-Y., LaRosa, G. & Gudas, L. J., *Dev. Biol.* 107:75-86 (1985).
60. Webster, N., Green. S. Jin, J. R., and Chambon, P., *Cell* 59:199-207 (1988) .
61. Weinberger, C., Hollenberg, S. M., Rosenfeld, M. G. & Evans, R. M., *Nature* 318:670-672 (1985).
62. Weinberger, C., Thompson, C. C., Ong, E. S., Lebo, R., Gruol, D. J. & Evans, R. M., *Nature* 324: 641-646 (1986).
63. Weinberger, C., Thompson, C. C., Ong, E. S., Lebo, R., Gruol, D. J., Evans, R. M., *Nature* 324, 641-646 (1986).
64. wigler, M. , et al., *Cell* 16:777-785 (1979) .
65. Wolback, S. B. & Howe, P. R., *J. Exp. Med.* 62:753-777 (1925).

SPECIFICATION SUMMARY

From the foregoing description, one of ordinary skill in the art can understand that the present invention provides substantially pure DNA which encodes the retinoid receptor protein referred to as retinoic acid receptor protein. The invention also provides a plasmid containing retinoic acid receptor DNA. This plasmid, phRAR1, has been deposited with the American Type culture Collection for patent purposes.

The invention is also comprised of retinoic acid receptor proteins, including modified functional forms thereof, expressed from the DNA (or mRNA) of the invention.

In addition to novel retinoic acid receptor DNA, RNA and protein compositions, the present invention includes chimeric hybrid receptors made by exchanging (1) the N-terminal domains, (2) the DNA-binding domains, and (3) the ligand-binding domains from hGR, hMR, hERR1, hERR2, $T_3R_\alpha$, $T_3R_\beta$, RAR$\alpha$, and RAR$\beta$ receptors with one another. The chimeric receptors so constructed have DNA-binding domain and ligand-binding domain characteristics similar to the DNA-binding domain and ligand-binding domain characteristics of the respective "parental" receptors from which they originated.

Finally, the present invention involves a bioassay for deter-mining the functional ligands for receptor proteins, both wild-type and chimeric.

The phRAR1 DNA of the invention can be used to make the retinoic acid receptor proteins, and functional modified forms thereof, in quantities that were not previously possible. The same is true of the chimeric receptors. With the quantities of receptor protein available as a result of the present invention, detailed studies can be made of both the ligand/receptor complexes and the ligand/receptor/HRE complexes. In addition, an adequate supply of the retinoic acid receptor proteins means that they can now be used to screen compounds for retinoic acid receptor-agonists or retinoic acid receptor-antagonist activity. Availability of the receptor proteins also means that they can be used in diagnostic assays to determine the levels of retinoic acid present in various tissues and body fluids.

Without departing from the spirit and scope of this invention, one or ordinary skill can make various changes and modifications to the invention to adapt it to various usages and conditions. As such, these changes and modifications are properly, equitably, and intended to be, within the full range of equivalence of the following claims.

What is claimed is:

1. An isolated protein, or functional fragment thereof, having a hormone binding and/or DNA binding domain of a retinoic acid receptor, wherein said protein is encoded by DNA capable of hybridizing with at least one polynucleotide having a sequence selected from the group consisting of the sequences shown in FIG. 1B-1 and 1B-2 under non-stringent hybridization conditions.

2. A protein according to claim 1 wherein said protein is human retinoic acid receptor.

3. A protein according to claim 2 encoded by DNA capable of hybridizing with at least one polynucleotide selected from the sequences shown in FIG. 1B-1 or 1B-2 under high stringency hybridization conditions.

4. A protein produced by expression, in receptor negative cells, of recombinant DNA encoding retinoic acid receptor, wherein said protein is encoded by DNA capable of hybridizing with at least one polynucleotide having a sequence selected from the group consisting of the sequences shown in FIG. 1B-1, and 1B-2 under non-stringent hybridization conditions.

5. A protein according to claim 4 wherein said protein is human retinoic acid receptor.

6. A protein according to claim 5 wherein said human retinoic acid receptor is selected from human retinoic acid receptor alpha or human retinoic acid receptor beta.

7. A protein according to claim 4 wherein said protein has a hormone binding and/or DNA binding domain of a retinoic acid receptor.

8. A protein according to claim 7 wherein said protein is human retinoic acid receptor.

9. A protein according to claim 8 wherein said human retinoic acid receptor is selected from human retinoic acid receptor alpha or human retinoic acid receptor beta.

10. A protein according to claim 4 wherein said recombinant DNA is selected from the group consisting of isolated DNAs having the nucleotide sequences shown in FIG. 1B-1, and 1B-2.

11. A protein according to claim 4 wherein said recombinant DNA is the retinoic acid encoding sequence of plasmid phRAR1 (ATCC No. 40,392).

12. A protein having the hormone binding and/or DNA binding domain of a retinoic acid receptor, wherein said protein is produced, in receptor negative cells, by expression of recombinant DNA capable of hybridizing with at least one polynucleotide having a sequence selected from the group consisting of the sequences shown in FIG. 1B-1, and 1B-2 under non-stringent hybridization conditions.

13. A protein according to claim 12 wherein said protein is human retinoic acid receptor.

14. A protein according to claim 13 wherein said human retinoic acid receptor is selected from human retinoic acid receptor alpha or human retinoic acid receptor beta.

* * * * *